US012456548B2

(12) United States Patent
Sudha et al.

(10) Patent No.: US 12,456,548 B2
(45) Date of Patent: Oct. 28, 2025

(54) SYSTEMS AND METHODS FOR GRAPHICAL USER INTERFACES FOR ADEQUACY OF ANESTHESIA

(71) Applicant: GE Precision Healthcare LLC, Milwaukee, WI (US)

(72) Inventors: Sai Sudha, Karnataka (IN); John D. Page, Madison, WI (US); Brandon Jacob Henak, Wauwatosa, WI (US); Sandeep S. Kurup, Karnataka (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 573 days.

(21) Appl. No.: 17/455,835

(22) Filed: Nov. 19, 2021

(65) Prior Publication Data

US 2023/0162842 A1 May 25, 2023

(51) Int. Cl.
*G16H 40/20* (2018.01)
*G16H 70/20* (2018.01)

(52) U.S. Cl.
CPC ............ *G16H 40/20* (2018.01); *G16H 70/20* (2018.01)

(58) Field of Classification Search
CPC .............................. G16H 40/20; G16H 70/20
USPC .............................................................. 705/2
See application file for complete search history.

(56) References Cited

U.S. PATENT DOCUMENTS

| | | | | |
|---|---|---|---|---|
| 2009/0076339 A1* | 3/2009 | Quintin | A61B 5/0205 600/301 |
| 2015/0133797 A1* | 5/2015 | Franz | A61B 5/0205 600/484 |
| 2017/0000412 A1* | 1/2017 | Scott | A61B 5/02055 |
| 2018/0082036 A1* | 3/2018 | Hanrahan | H04L 65/762 |
| 2018/0193579 A1 | 7/2018 | Hanrahan | |
| 2019/0371456 A1* | 12/2019 | Page | G16H 10/60 |
| 2020/0197641 A1* | 6/2020 | Hanrahan | G16H 15/00 |

FOREIGN PATENT DOCUMENTS

CN 111407967 A 7/2020

OTHER PUBLICATIONS

Choi, B. M., Shin, H., Lee, J. H., Bang, J. Y., Lee, E. K., & Noh, G. J. (2021). Performance of the surgical pleth index and analgesia nociception index in healthy volunteers and parturients. Frontiers in Physiology, 12, 554026. (Year: 2021).*

(Continued)

*Primary Examiner* — Mamon Obeid
*Assistant Examiner* — Winston Furtado
(74) *Attorney, Agent, or Firm* — McCoy Russell LLP

(57) ABSTRACT

Systems and methods are provided for perioperative care in a medical facility. In an example, a system includes a display and a computing device operably coupled to the display and storing instructions executable to: determine each of an Adequacy of Anesthesia (AoA) protocol usage and an AoA protocol compliance based on medical device data received from one or more medical devices and parameters for an AoA protocol; and output, to the display, a graphical user interface (GUI) that includes an AoA protocol usage indication generated based on the determined AoA protocol usage and an AoA protocol compliance indication generated based on the determined AoA protocol compliance.

18 Claims, 9 Drawing Sheets

(56) References Cited

OTHER PUBLICATIONS

N/A. (Aug. 2021). Carestation Insights Analytics Applications. GE, 1-14. https://www.gehealthcare.com/products/anesthesia-delivery/carestation-insights. (Year: 2021).*

N/A. (Sep. 2021). Carestation Insights Adequacy of Anesthesia (AoA) Application. GE, 1-8.https://landing1.gehealthcare.com/rs/005-SHS-767/images/45351-AOA-6-1-Carestation-Insights-Adequacy-LP-PM.pdf. (Year: 2021).*

N/A. (Aug. 2021). Carestation Insights Analytics Applications. GE, 1-14 (Year: 2021).*

N/A. (Sep. 2021). Carestation Insights Adequacy of Anesthesia (AoA) Application. GE, 1-8. (Year: 2021).*

EP application 22206353.9 filed Nov. 9, 2022—Search Report issued Apr. 18, 2023; 10 pages.

* cited by examiner

SYSTEMS AND METHODS FOR GRAPHICAL USER INTERFACES FOR ADEQUACY OF ANESTHESIA

FIELD

Embodiments of the subject matter disclosed herein relate to patient monitoring during perioperative care, and more specifically to simultaneously monitoring anesthesia usage across operating rooms and over time.

BACKGROUND

Certain medical procedures, such as surgery, may include performing certain sub-procedures to prep the patient for surgery, maintain the patient in a certain condition during surgery (e.g., anesthetized), and help the patient recover after surgery. Such sub-procedures that are performed in support of a main procedure may be referred to as perioperative care. Perioperative care of patients in a hospital or other medical facility may include multiple patient monitoring devices that monitor parameters such as neuromuscular transmission (NMT), surgical plethysmographic index (SPI), mean arterial blood pressure (MAP), etc. As one example, the patients may be treated with inhaled and intravenous hypnotics, opioids, and/or neuromuscular blocking agents (NMBAs), and the patient monitoring devices may help care providers (e.g., clinicians) assess each patient's individual response to such agents. However, without aggregated data, it may be difficult to identify trends in anesthesia usage and resulting patient outcomes that may reduce agent usage, increase productivity, and increase positive patient outcomes.

BRIEF DESCRIPTION

In one aspect, a system comprises a display, and a computing device operably coupled to the display and storing instructions executable to: determine each of an Adequacy of Anesthesia (AoA) protocol usage and an AoA protocol compliance based on medical device data received from one or more medical devices and parameters for an AoA protocol; and output, to the display, a graphical user interface (GUI) that includes an AoA protocol usage indication generated based on the determined AoA protocol usage and an AoA protocol compliance indication generated based on the determined AoA protocol compliance.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1A:
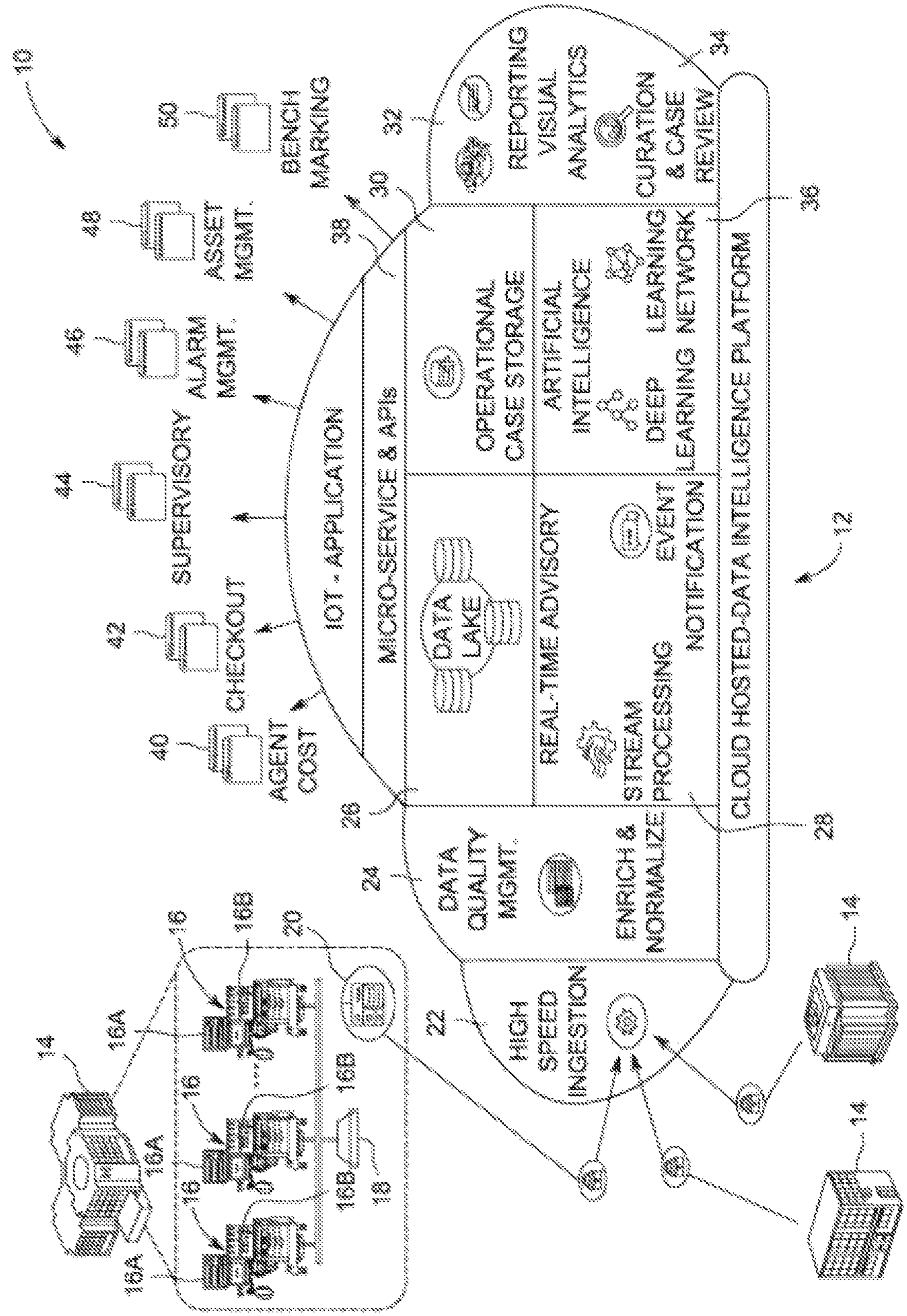
FIGS. 1A and 1B schematically show an example system for perioperative care and supervision including an Adequacy of Anesthesia (AoA) application.

Embodiments of the present disclosure will now be described, by way of example, with reference to the FIGS. 1A-7, which relate to various embodiments for facilitating perioperative care for a plurality of patients. To facilitate the perioperative care described herein, the systems and methods as disclosed herein collect and process a wide variety of medical device data. The medical device data includes physiological data (also referred to as patient monitoring data) that is acquired from a patient by a medical device and machine data collected internally from the medical device itself, such as the medical devices shown in FIGS. 1A and 1B. The machine data may include alarms, device status, settings, messages, and measured operational data. The machine data may further include settings and values that represent specific actions taken with the medical device, for example, in response to automated controls or due to clinician inputs. For example, in an anesthesia delivery machine, this may include changes to oxygen, gas flow rates, and/or anesthetic agent concentrations. The machine data may further include clinical and/or technical alarms initiated by the medical device or device diagnostic information. Still further examples of the machine data include proactive or predictive service alerts from the medical device, maintenance checkout information, and/or processor clock cycle signals or power signals or other operational signals from various components of the medical device indicative that the medical device is turned on, in use, in operation, held in a stand by condition, or turned off.

The medical device data can be collected in a time series format as provided from the medical devices themselves. As used herein, the time series format of the medical device data can include waveforms, binary data, numeric data, and/or textual data in a time series format. Embodiments of the systems and methods as disclosed herein receive the medical device data from the medical devices at a frequency similar to the frequency at which it is produced by the medical device. In embodiments, this increased velocity of the received data and the monitoring and analysis of the medical device data may enable the real-time monitoring systems and methods disclosed herein. As used herein, the term "real-time" may refer to processes executed without intentional delay.

As described in further detail herein, the medical device data may undergo real-time analysis for Adequacy of Anesthesia (AoA). AoA is a concept that helps clinicians deliver an individually tailored anesthetic agent amount to each patient. According to embodiments described herein, clinicians may assess each patient's individual response to inhaled and intravenous hypnotics, opioids, and neuromuscular blocking agents (NMBAs) using neuromuscular transmission (NMT), a surgical plethysmographic index (SPI), and entropy parameters via an AoA application. The AoA application may provide visibility to the usage of these parameters across different operating rooms in a healthcare facility (e.g., a hospital) via a graphical user interface (GUI). By analyzing the medical device data, a phase of each of the ongoing cases may be shown along with current values of anesthesia monitoring parameters. For example, the patient monitoring data and the machine data may be combined and/or used together in algorithms to generate feedback to the clinicians to drive changes to an AoA protocol and to track the corresponding outcomes. Further, all of the medical device data may be saved for retrospective and automated machine learning and analysis.

Figure 2:
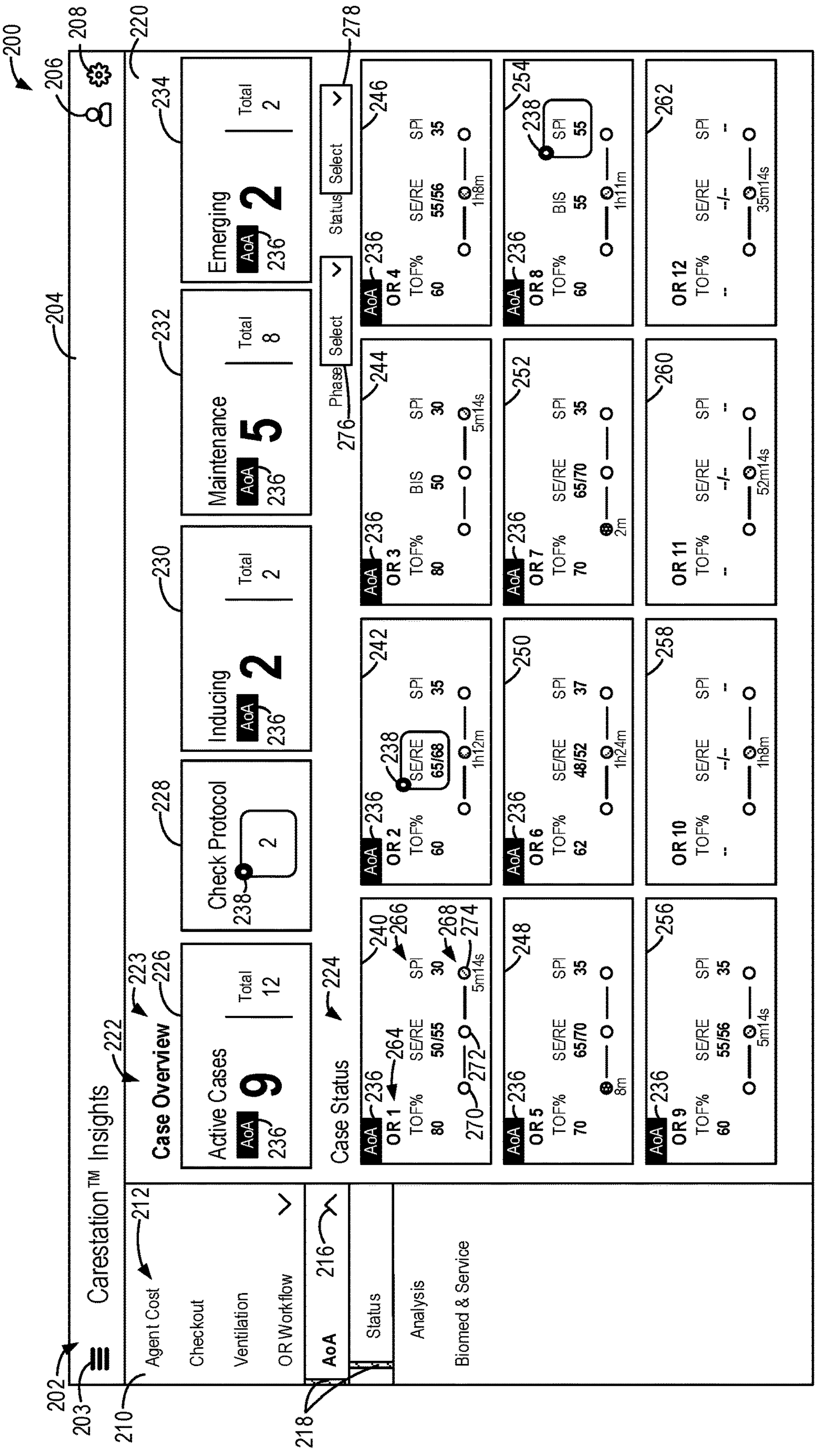
FIG. 2 shows an embodiment of an AoA status dashboard generated via the AoA application.

The AoA application may facilitate a display of real-time data for a plurality of patients and for a plurality of different anesthesia monitoring parameters, such as via the AoA status dashboard FIG. 2. The displayed anesthesia monitoring parameters for the plurality of patients may be displayed simultaneously in a multi-patient GUI, which may allow a supervising care provider to easily monitor a patient status and AoA protocol usage and compliance for each operating room, even if the care provider is located away from the operating room(s). When additional information for a specific operating room or date range is desired, the AoA application may generate an overview within the GUI that provides a more detailed analysis using historical data, such as via the AoA analysis dashboard of FIGS. 3 and 4 and according to the method of FIGS. 6A and 6B. Further, the AoA application may provide an interface for configuring the AoA protocol, such as via the AoA administration dashboard of FIG. 5 and via the method of FIG. 7. In this way, the AoA application may provide readily accessible insights on the tailored anesthesia protocol and the impacts that the healthcare facility may achieve with the tailored AoA monitoring. As a result, healthcare costs may be decreased while patient outcomes are increased.

Figure 1B:
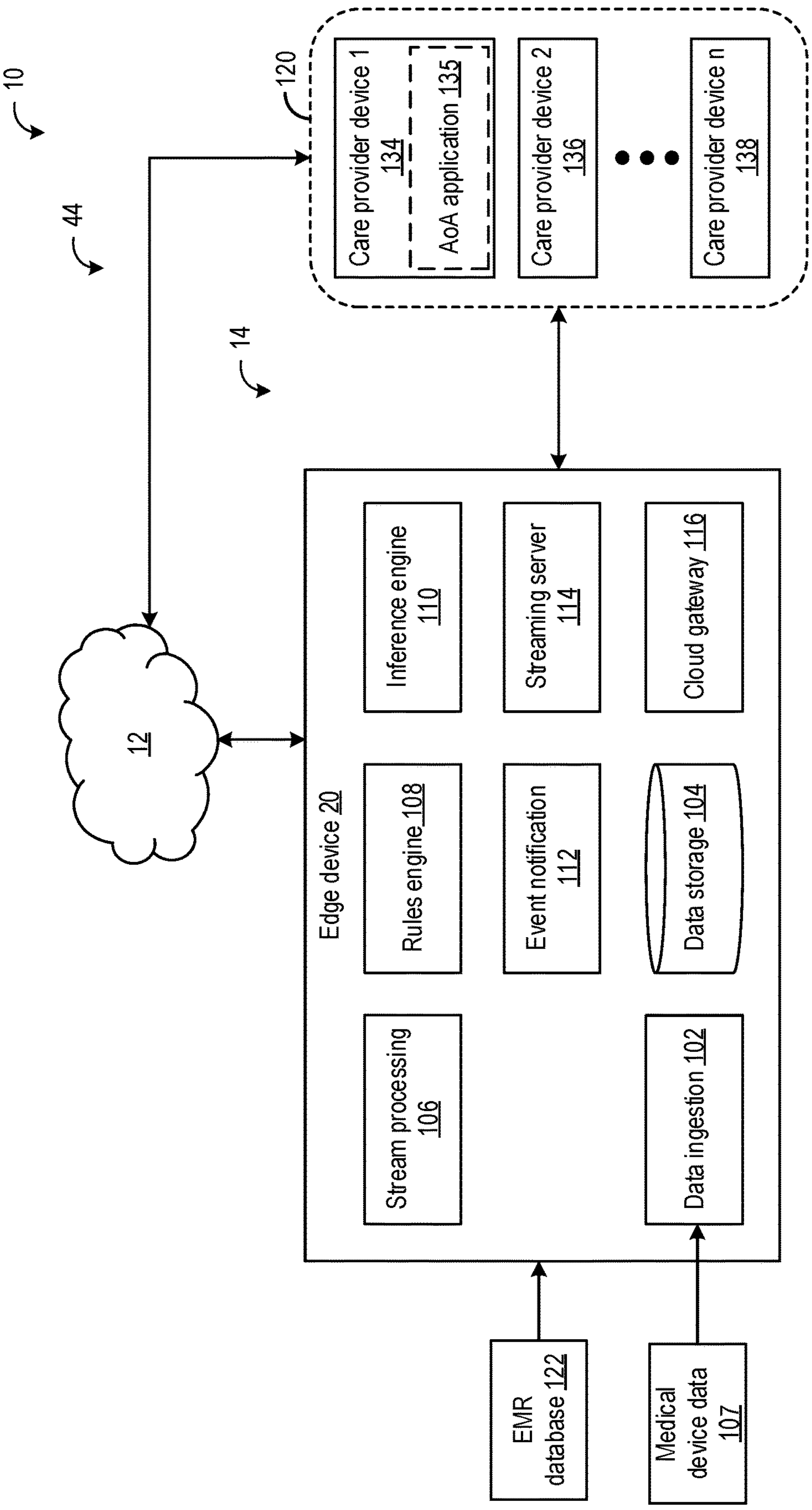

Turning now to the figures, FIGS. 1A and 1B depict an exemplary embodiment of a system 10 for perioperative care and supervision. Referring first to FIG. 1A, the system 10 includes a medical device data (MDD) processing system 12. The MDD processing system 12 may include a variety of hardware and/or software implementations and it should be noted that such implementations are not considered to be limiting. For example, it is contemplated that any or all of the MDD processing system 12 may be embodied exclusively in hardware, exclusively in software, exclusively in firmware, or in any combination of hardware, software, and/or firmware. While the following describes exemplary methods and systems, the examples provided herein are not the only way to implement such methods and systems.

In embodiments wherein any of the claims are read to cover an entirely software and/or firmware implementation, in any embodiment, at least one of the elements is hereby expressly defined to include a tangible and non-transient computer readable medium. As used herein, the term tangible computer readable medium is expressly defined to include any type of computer readable storage and to exclude propagating signals. Additionally or alternatively, the example methods and systems may be implemented using coded instruction (e.g., computer readable instructions) stored on a non-transitory computer readable medium such as a flash memory, a read-only memory (ROM) a random-access memory (RAM), a cache, or any other storage media in which information is stored for any duration (e.g., for extended period time periods, permanently, brief instances, for temporarily buffering, and/or for caching of the information). As used herein, the term non-transitory computer readable medium is expressly defined to include any type of computer readable medium and to exclude propagating signals.

In exemplary and non-limiting embodiments of the medical device data processing system 12, the MDD processing system 12 is implemented by one or more networked processors or computing devices. The MDD processing system 12 may be implemented in a cloud computing platform and/or infrastructure. Memory and processors as referred to herein can be standalone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

The MDD processing system 12 is communicatively connected to at least one hospital network 14. Such communicative connections as well as the hospital network itself may include, but are not limited to, a wide area network (WAN); a local area network (LAN); the internet; a wired or wireless (e.g., optical, Bluetooth, radio frequency) network; a cloud-based computer infrastructure of computers, routers, servers, gateways, etc.; or any combination thereof associated therewith that allows the system or portions thereof to communicate with one or more computing devices.

The hospital network 14 may exemplarily be a network associated with a portion of a hospital, for example a surgery unit or department of a hospital, or may be more broadly located across medical devices of an entire hospital. It further will be recognized that while some embodiments and implementations of the systems and methods as disclosed herein may seek to operate on a single hospital or unit of a hospital, still other embodiments may connect a plurality of hospital networks, including hospitals currently owned or operated or otherwise affiliated with one another. In still further embodiments, while individual hospitals or groups of hospitals may use the MDD processing system 12, the MDD processing system 12 may receive and process information from a plurality of hospital networks including those unaffiliated with one another at the same time.

As depicted in FIG. 1A, the hospital network 14 includes a plurality of medical devices 16. The medical devices 16 may include physiological monitoring devices 16*a* as well as patient therapy devices 16*b*. The physiological monitoring devices 16*a* may include, but are not limited to, heart rate monitors, blood pressure monitors, blood oxygenation monitors, respiration monitors, electrocardiogram (ECG) monitors, electroencephalogram (EEG) monitors, and electromyography (EMG) monitors. An exemplary embodiment of an anesthesia delivery machine will be described as an exemplary embodiment of the medical device 16, and more specifically as the patient therapy device 16*b*, although it may be understood that other devices, including but not limited to patient respiratory assistance devices or dialysis machines, may be further non-limiting examples of patient therapy devices. However, it will be recognized that therapy devices may also include capabilities to not only deliver patient therapy, but also to measure physiological parameters of a patient. For example, embodiments of anesthesia delivery machines may include gas analysis modules operable to measure gas concentrations expired by the patient. In some embodiments, imaging devices, including but not limited to x-ray, computed tomography (CT), magnetic resonance imaging (MRI), and ultrasound devices, may be examples of the medical devices 16 as contemplated within the present disclosure. Still further examples of medical devices may include video and/or audio recording devices.

In an exemplary embodiment, at least a portion of the MDD processing system 12 as described herein may be implemented locally, for example as an anesthesia delivery management system 18. In such an embodiment, the anesthesia delivery management system 18 may operate to collect medical device data from a plurality of patient therapy devices 16*b* inter alia to monitor anesthesia agent use between anesthesia delivery machines and across procedures performed by the anesthesia delivery machines in an effort to visualize anesthetic agent consumption and use as well as to quantify, monitor, and evaluate trends across all of the anesthesia delivery machines in the hospital or surgical unit, such as using the AoA application further described herein.

The medical devices 16 may be communicatively connected to one or more edge devices, such as an edge device 20. The edge device 20 may exemplarily be an edge processing device, a cloud processing device, or an internet gateway. The edge device 20 may include an internet of things (IOT) gateway which facilitates a secure communications link between the medical devices 16 at the hospital network 14 with the servers, processors, and computer readable media implementing the MDD processing system 12. In exemplary embodiments, the edge device 20 may communicate directly with one or more of the medical devices 16. In other examples, the edge device 20 may communicate with the medical devices 16 through an intermediate network, such as the anesthesia delivery management system 18 or another medical device data system or network.

The edge device 20 receives the medical device data as time series data for any of the medical device data available from the medical devices. As noted above, the data streams of the medical device data (e.g., machine data, monitored patient physiological parameter data) are available in a time series format as acquired from the medical devices and may include, but are not limited to, time series information of alarms, device status, device settings, messages, and measured data. In embodiments, the medical devices may be equipped with sensors that increase a self-awareness of the medical device, such as sensors that monitor the function, inputs and/or outputs of various components of the medical device itself. Many such sensors may be incorporated into medical devices to measure compressor speeds and/or cycle times, internal pressures, voltages, clock speeds, temperatures, etc.

The edge device 20 encrypts the time series formatted data, and the encrypted data is transmitted using wired and/or wireless communication techniques for encrypted data to the server, processors, and data storage carrying out the MDD processing system 12. The edge device 20 continuously transmits de-identified medical device data in the time series format over an encrypted communication channel to a high speed data ingestion module 22 of the MDD processing system 12. While the exemplary embodiment described herein may reference de-identified data, it will be recognized that other embodiments may use patient-identified data with appropriate security considerations for handling patient data. The high speed data ingestion module 22 takes in the real-time streams of the medical device data. The data ingestion can be performed in an automated fashion and can preprocess the received streams of real-time data in the time series for later processing by the MDD processing system 12. The high speed ingestion module 22 can receive concurrent data streams from multiple connected devices across multiple sites at a high incoming velocity, for example at or near the frequency at which medical devices can output data. In exemplary embodiments, the high speed ingestion module 22 is scalable to continue to ingest increased bandwidth of medical device data without significant decrease in ingestion speeds.

The high speed ingestion module 22 takes the time series medical device data from the medical devices of one or more hospital networks and formats it for further processing by a data quality management module 24. In exemplary and non-limiting embodiments, the high speed ingestion module 22 supports an open standard such as ASTMF 2761 or integrated clinical environmental (ICE). The data quality management module 24 may normalize, enrich, and tag the data streams without negatively impacting data latency. In a healthcare environment, a variety of healthcare information products and/or systems may be used to provide medical services, collect medical data, conduct medical exams, etc. However, many healthcare information systems operate using various messaging standards (e.g., Health Level 7 International (HL7 V2.x/v3), Clinical Document Architecture/Continuity Of Care Document (CDA/CCD), American Society for Testing Materials (ASTM), Digital Imaging and Communications in Medicine (DICOM), etc.) and various standards and/or protocols (e.g., cross-enterprise document sharing (XDS.A/B), cross-enterprise document media interchange (XDM), cross-enterprise document reliable interchange (XDR), patient identifier cross-referencing/patient demographics query (PIX/PDQ), patient administration management (PAM), query for existing data (QED), national counsel for prescription drug programs (NCPDP), etc.) that make system integration and/or communication more difficult. Thus, the normalization may include reformatting of the medical data to a consistent or compatible format for use within the MDD processing system 12. In an exemplary embodiment, the medical device data may be normalized into the ISO/IEEE 11073-10101 nomenclature and its extensions. In a still further exemplary embodiment, the data quality management module 24 may normalize the streams of the incoming time series data by converting units of measure. The data quality management module 24 may further operate to identify and tag various types of medical device data, locations from which the medical device data was received, or time series data streams originating from the same medical device. These tags may be used as further detailed herein to identify and analyze groups of streams of the time series data.

In an exemplary embodiment, the data quality management module 24 normalizes the received incoming data by transforming and/or translating the clinical data streamed from the source healthcare system or device into a canonical data model with associated metadata. The processed medical device data is stored in a data lake 26, which is exemplarily implemented in computer readable storage embodying capability to store terabytes of data. The data lake 26 is a long-term computer storage repository that holds large amounts of raw data in a native format until the data is needed. The native format may include the time series data from the medical devices, which may be in waveform or binary format, audio data, image data, and/or video data. In embodiments, the data lake 26 may help to facilitate the ingestion of the data that may not be processed in real-time but may still be taken in in real-time or near real-time and instead stored until analysis or usage is desired. This may be facilitated by identifying particular data streams and limiting the processing of those data streams, for example, by the data quality management module 24, if it is known at that time that such data stream is not being used in real-time analysis. In an exemplary embodiment, the data quality management module 24 may not convert the data to a canonical data model but may still attempt to tag, enrich, or index the data to facilitate later retrieval of that data from the data lake 26 in a standardized manner.

In a still further embodiment, portions of the data that are stored in the data lake 26 may also be additionally stored in a graph database which may be a separate database residing on the same computer readable storage, or may be embodied on separate computer readable storage from the data lake 26. The graph database may receive the data streams of which it is known that the system may analyze trends in that data stream. The graph database may store the streams of data in the time series format in a way that facilitates trending of the data over time and appending the data with events either identified in the data itself, in one or more of the other data streams, or received by the system from an external source. These events may include, but are not limited to, medical device or clinician actions, clinical events, situations, or complications that arise during the medical procedure. The graph database may later be used by a clinician or technician to identify further relationships between trends and the data streams with other analysis as disclosed herein.

At the same time that the data is stored in the data lake 26, the enriched and normalized medical device data may be provided to a stream processing engine 28. The stream processing engine 28 identifies cases and events in the time series streams of medical device data. Identified clinical cases may be stored in an operational case database 30. The clinical cases may exemplarily include surgical and intensive care unit (ICU) cases. The clinical cases may be identified by the medical device used and the timing of the medical data in the time series of the medical device data. For example, a time series of medical device data from an anesthesia delivery machine showing a change in status from the machine being powered on and followed by changes to device settings and delivery and/or consumption of anesthetic agent all indicate that a clinical case has begun or is ongoing.

As noted above, the streams of the time series medical device data originating from the same medical device or from the same location in a hospital may be tagged or otherwise identified as being related. These tags may be used to simultaneously analyze related data streams or combine analysis of related data streams to identify clinical cases. For example, a device status data stream analysis may be combined with a user input data stream, device setting data stream, and operational data streams to identify when the device is used and how it is used in the clinical case. This information may help to distinguish between a maintenance or checkout of the medical device by a technician from the use of the device for clinical case.

The analysis of the data streams of multiple medical devices, particularly those identified as being related or co-located may further be used to identify clinical cases. For example, coordinated or similar actions in data streams of an anesthesia delivery device and a related patient monitoring device, and/or respiratory support device and/or imaging device, etc., may further be used to identify that these devices are being used together for a clinical case. In still further embodiments, the streaming time series of the medical device data may be combined with information regarding scheduled clinical cases to help to further identify when and how the medical devices are used during clinical cases.

In embodiments, knowledge of a scheduled use of the medical device (e.g., the anesthesia delivery machine) can be used to further identify clinical cases in the streams of medical device data. For example, input or received knowledge regarding a type and time of a scheduled procedure may help to identify the start and end of the clinical case in particular streams of medical device machine data. In an embodiment, a known schedule of use for the medical device may help to identify clinical cases from maintenance or calibration actions which may similarly power up and at least partially operate the medical device.

The medical device data associated with the actions of the anesthesia delivery device and/or other medical devices during the identified clinical case may be stored in the operational case database 30. In an example, the identification of the clinical case is stored along with the other time series streams of medical device data from that anesthesia delivery machine as well as time series streams of medical device data from any physiological monitors and/or other medical devices associated with the use of that anesthesia delivery machine. In another exemplary embodiment as described in further detail, a clinical case summary with links or identifiers to the associated time series medical device data stored in the data lake 26 can be created and stored in the operational case database 30.

In an embodiment, prior to storing the clinical cases in the operational case database 30, the clinical cases may be classified or profiled, which is a technique used for data curation. The profiling of the clinical cases may be based upon, in part, the information in the clinical case summary, and as described in further detail herein, may be used to group the clinical cases into groups, for example, normal cases, edge cases, and outlier cases. These determinations may be made in view of a comparison between the time series data in the clinical case against normal distributions of the same type of time series machine data in other similar clinical cases. Edge cases may be identified as borderline or ambiguous cases, not clearly defined as either normal or an outlier. In an illustrative, exemplary embodiment, for a particular measured value or occurrence, a distribution of such occurrences may be used to establish normal, edge, and outlier cases. In another illustrative, exemplary embodiment, a normal case may be within a standard deviation of a median value in the normal distribution, while edge cases are between one and two standard deviations and outlier cases are greater than two standard deviations from the median. The categorized cases may be further investigated to create or increase an accuracy of event detection algorithms, rules for clinical decision support, alert algorithms, and predictive algorithms.

The stream processing engine 28 also identifies events in the time series streams of medical device data, for example in the manners as described in further detail herein, and presented in a reporting and visual analytics tool 32, which exemplarily may be presented on a graphical display communicatively connected to the medical device data processing system 12. For example, the reporting and visual analytics tools 32 may be included in the AoA application that will be further described herein.

Once clinical cases are stored in the operational case database 30, clinical cases may be reviewed manually by a clinician or technician using a curation and case review tool 34. The curation and case review tool 34 may be presented in a graphical user interface on a graphical display and further provide inputs exemplarily through the graphical user interface for the user or technician to curate or otherwise assess the clinical cases. This can be performed for investigative, educational, and data curation purposes.

The reporting and visual analytics tool 32 may present the detected events in a variety of channels of communication. For example, the detected events may be presented visually through graphical user interfaces and graphical displays. The detected events or notifications of the detected events can also be reported by communication of events/event notifications to wearable or mobile devices and presentation of medical device data and identified events in visual form in reports and/or dashboards presented in a graphical user interface on a graphical display, as will be explained in more detail below.

The results of the streaming analytics and event detection in the time series of medical device data may be provided to an application programming interface (API) 38 for use by application developers to provide monitoring, reporting, and/or control applications based upon the analyzed streams of medical device data. Such applications may operate through a computer operating system, a website browser, or operate on a mobile computing device or wearable computing device. Non-limiting examples of applications that may leverage the analysis of the time series medical device data include, but are not limited to, an anesthetic agent cost dashboard 40, a checkout dashboard 42, a supervisory application 44, an alarm management application 46, an asset management application 48, and a benchmarking application 50. At least a portion of these applications may be included within the AoA application discussed herein.

The agent cost dashboard 40 may present medical device data regarding anesthetic agent use for individual clinical cases, across clinical cases, as well as between anesthesia delivery machines within a hospital network or comparatively between hospital networks. By comparatively presenting this information, anesthetic agent use and behavioral changes can be understood and undertaken to promote efficient use of anesthetic agent, such as by developing and/or adjusting AoA protocols.

The checkout dashboard 42 may assist in monitoring the inspection and maintenance of the monitored medical devices. Medical device data such as device status and settings, as well as messages and information in machine data, may provide insight into the inspection processes for maintaining medical devices at a hospital network. The checkout dashboard 42 may identify maintenance and/or testing events in the streams of machine data and note these identified testing events against a testing schedule, requirement (e.g., daily), or other criterion.

The supervisory application 44 may be used by attending and/or supervising anesthesiologists to more efficiently manage remote personnel, nurse anesthetists, and/or other care providers simultaneously working across multiple locations or theatres. The alarm management application 46 may report and present medical device data regarding alarm notifications and silences of alarm notifications in order to better understand and adjust alarms to improve signal to noise in alarm events and to reduce alarm fatigue by clinicians.

The asset management applications 48 may present use, status, maintenance, and/or inspection information regarding medical devices (e.g., anesthesia delivery machines) or consumables used by medical devices, including components that may be frequently replaced, refilled, or refurbished during normal operation of the medical device (e.g., filters, absorbers). The benchmarking application 50 may provide further operational and quality performance data across providers and/or organizations or in a comparative manner.

The supervisory application 44 allows for qualified users (e.g., clinicians such as anesthesiologists, nurses, and other care providers) to view ventilator, anesthesia, and vital parameters of a plurality of patients in different locations (e.g., in different operating rooms) on various smart phones, tablets, or other computing devices associated with the qualified users. The supervisory application 44 may include a backend that is hosted on the edge device 20 and/or the MDD processing system 12 as dockers/micro services and may be rendered on a user's device (such as a care provider device 134 shown in FIG. 1B) using a suitable visualization platform. Further, the supervisory application 44 may be included in the AoA application to allow the qualified users to configure the AoA protocol, as will be elaborated below.

FIG. 1B schematically shows example devices of the system 10 via which an AoA application 135 may be executed, including the edge device 20 in communication with a plurality of care provider devices 120 via the hospital network 14 and also in communication with the MDD processing system 12.

As mentioned above, the edge device 20 receives medical device data 107 from the medical devices 16. The medical device data 107 received by the edge device 20 may be ingested by a data ingestion module 102, which may be similar to the ingestion module 22 of FIG. 1A, and stored in a data storage 104. The data storage 104 may be an ephemeral datastore where the received data is stored temporarily rather than persistently. For example, the received data, such as the medical device data 107, may be sent to the MDD processing system 12 for long-term storage. Further, the received medical device data 107 may be allocated to various micro services on the edge device 20 in order to carry out aspects of the AoA application 135, including a stream processing module 106, a rules engine 108, an inference engine 110, an event notification service 112, a streaming server 114, and a cloud gateway 116.

Figure 5:
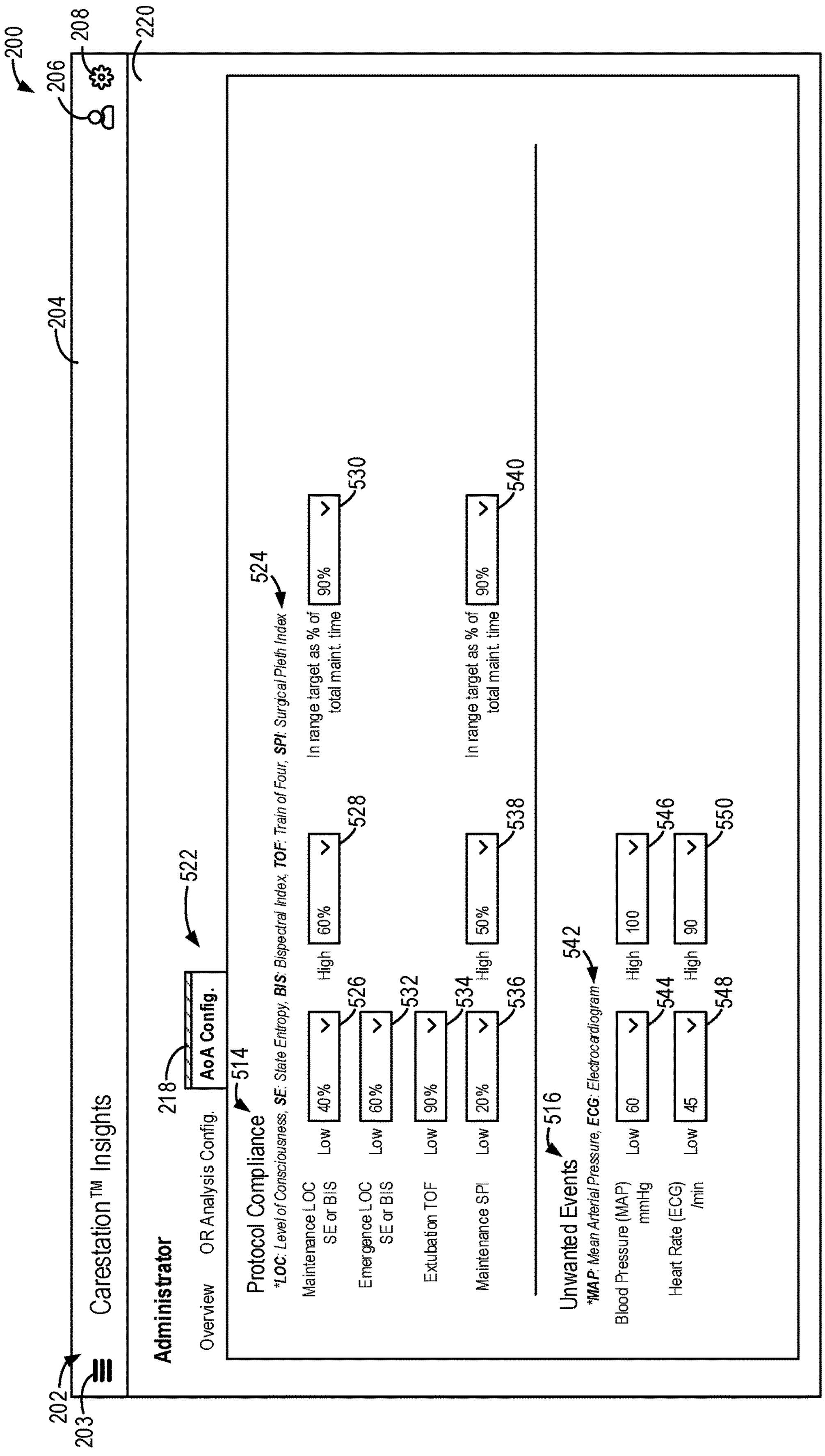
FIG. 5 shows an exemplary AoA administration dashboard generated via the AoA application, according to an embodiment.
Figure 6A:
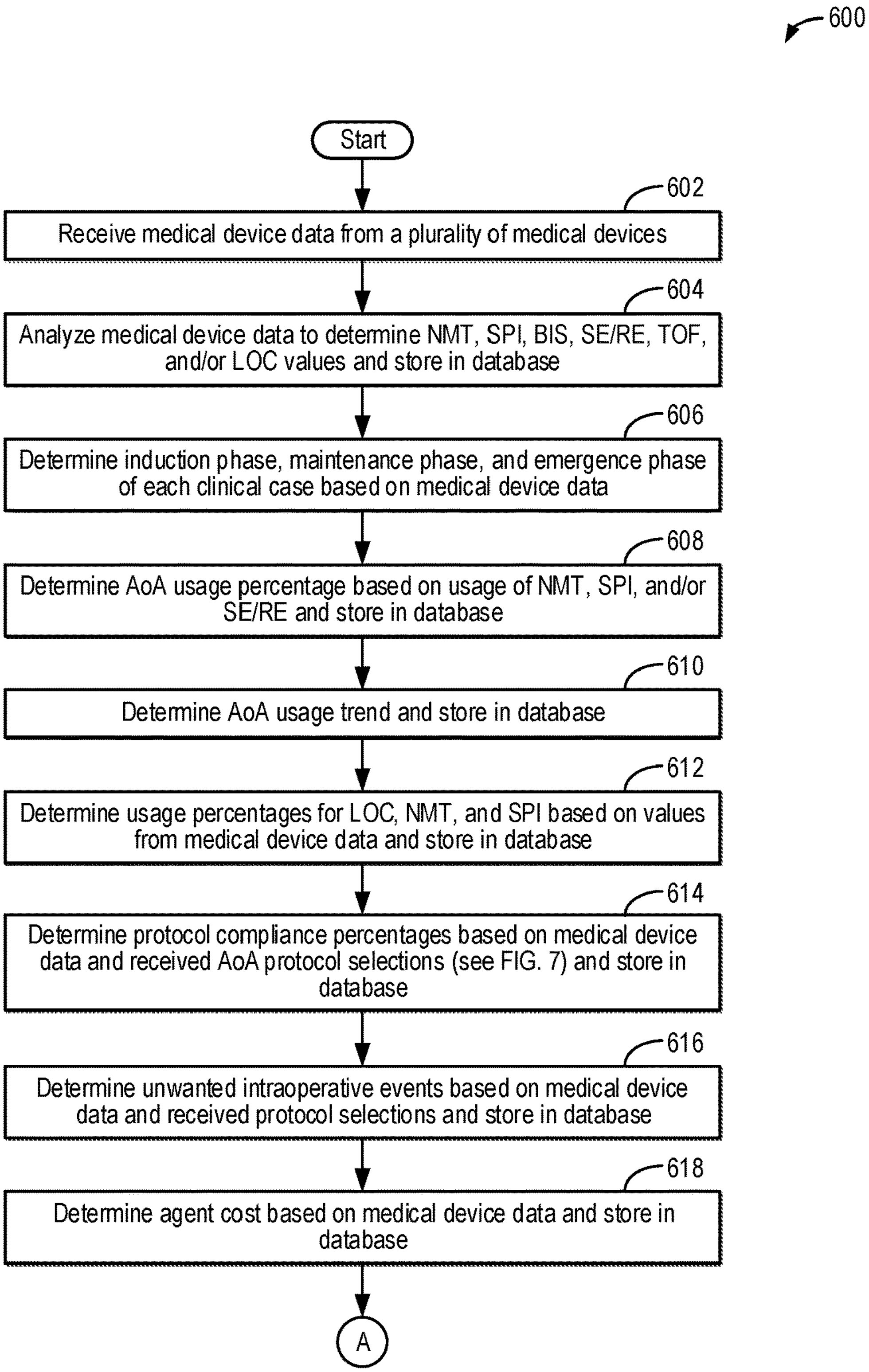
FIGS. 6A and 6B show a flow chart for an example method for analyzing and outputting anesthesia parameter data via the AoA application.
Figure 6B:
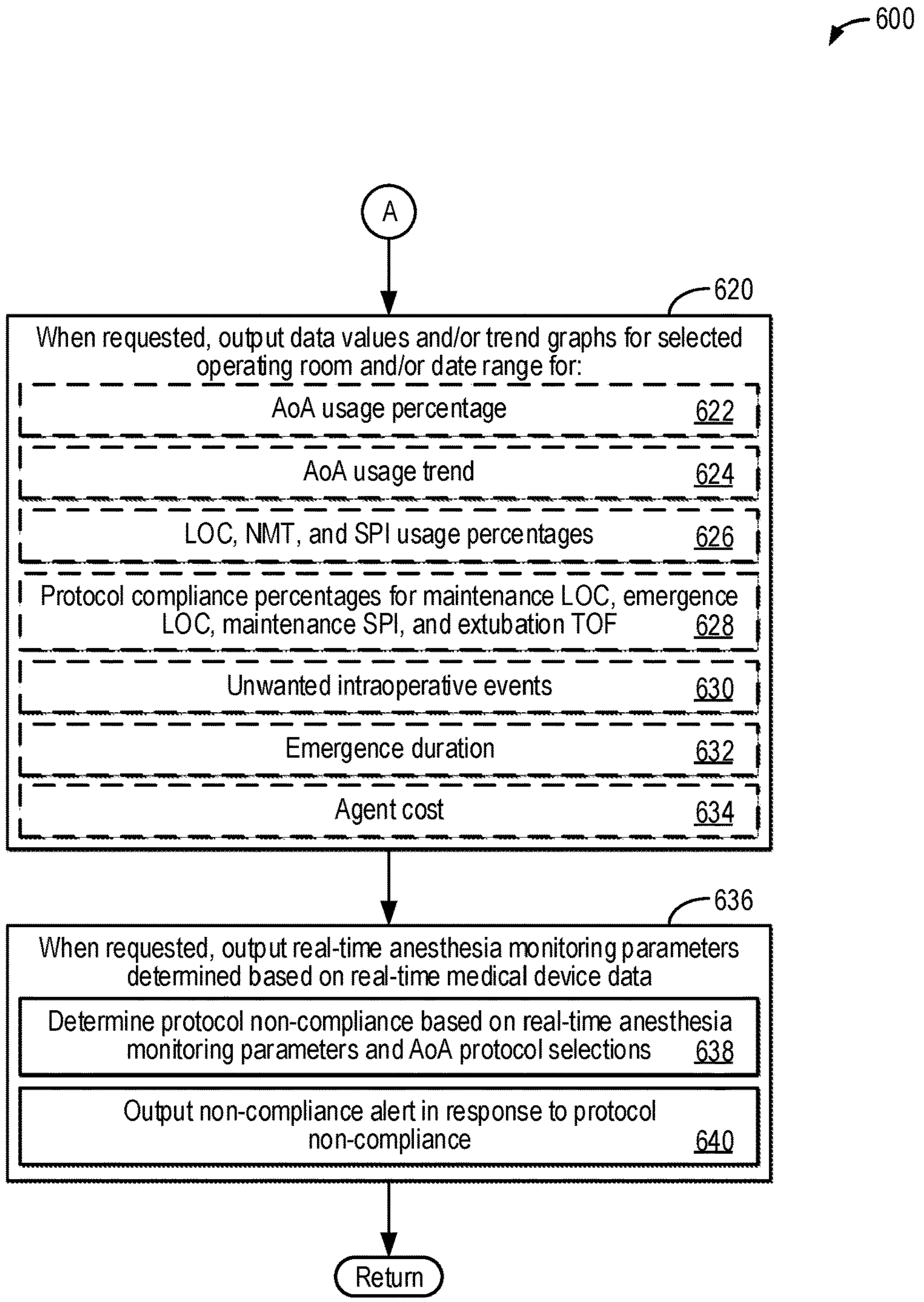

As explained above, the AoA application 135 may be used by attending and/or supervising anesthesiologists to manage other care providers, such as nurse anesthesiologists and/or other subordinate care providers, and to identify care providers who are using and complying with an AoA protocol versus those who are not, such as will be further described with respect to FIGS. 2 and 6A-6B. The AoA application also enables the attending and/or supervising anesthesiologists to compare a cost, duration, and number of unwanted events for clinical cases compliant with the AoA protocol versus non-compliant cases, such as will be described below with respect to FIGS. 3-4 and 6A-6B. As another example, the AoA application may enable the attending and/or supervising anesthesiologists to adjust the AoA protocol, such as will be described below with respect to FIGS. 5 and 7.

For example, via the AoA application 135, the user may toggle between different windows (or dashboards) of a graphical user interface (GUI). For example, each window/ dashboard may include a specific layout of patient-related or protocol-related information. Some information may not be shown unless the corresponding dashboard is selected. For example, an AoA status dashboard may show real-time patient information for a plurality of clinical cases, as will be described with respect to FIG. 2, while an AoA analysis dashboard may show non real-time data and data trends derived from analyzing historic patient information, as will be described with respect to FIGS. 3 and 4. Further, an AoA administration dashboard may enable the user to configure the AoA protocol. The user may customize which operating rooms to view, which patient monitoring parameters to view, which alarms and insights to apply, and other parameters of the GUI dashboards used to present the above-described information, such as a layout of each graphical user interface.

The GUI dashboards that are generated via the supervisory application 44 may be displayed on one or more suitable display devices associated with a respective care provider device and/or medical facility administration device. As shown in FIG. 1B, a plurality of care provider devices 120 may be included as part of the hospital network 14, from a first care provider device 134, a second care provider device 136, and on up to an nth care provider device 138, and may be communicatively coupled to the edge device 20 via the hospital network 14. Each care provider device may include a processor, a memory, a communication module, a user input device, a display (e.g., screen or monitor), and/or other subsystems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility and substantially fixed in place (such as in a nurse's station or in the room of a patient) and/or located locally or remotely from the medical facility and configured to move with the care provider (such as a care provider's mobile device).

When viewing graphical user interfaces generated via the AoA application 135 via a display of a care provider device, a care provider may enter inputs (e.g., via the user input device, which may include a keyboard, mouse, microphone, touch screen, stylus, or other device) that may be processed by the care provider device and sent to edge device 20. In examples where the user input is a selection of a link or user interface control button, the user input may trigger progression to a desired view or state of the graphical user interface (e.g., trigger the display of a desired dashboard, layout, desired data, etc.), trigger updates to the configuration of the graphical user interface or AoA protocol, trigger settings to be saved, trigger changes to a machine (such as an anesthesia delivery machine), or other actions.

The devices disclosed herein, such as the care provider devices and/or aspects of the edge device 20, may each include a communication module, memory, and processor(s) to store and execute aspects of the AoA application 135 as well as send and receive communications, graphical user interfaces, medical data, and other information.

Each communication module facilitates transmission of electronic data within and/or among one or more systems. Communication via the communication module can be implemented using one or more protocols. In some examples, communication via the communication module occurs according to one or more standards (e.g., DICOM, Health Level Seven (HL7), ANSI X12N, etc.). The communication module can be a wired interface (e.g., a data bus, a Universal Serial Bus (USB) connection, etc.) and/or a wireless interface (e.g., radio frequency, infrared, near field communication (NFC), etc.). For example, a communication module may communicate via a wired local area network (LAN), a wireless LAN, a wide area network (WAN), etc. using any past, present, or future communication protocol (e.g., BLUETOOTH®, USB 2.0, USB 3.0, etc.).

Each memory may include one or more data storage structures, such as optical memory devices, magnetic memory devices, or solid-state memory devices, for storing programs and routines executed by the processor(s) to carry out various functionalities disclosed herein. Memory may include any desired type of volatile and/or non-volatile memory such as, for example, static random access memory (SRAM), dynamic random access memory (DRAM), flash memory, read-only memory (ROM), etc. The processor(s) may be any suitable processor, processing unit, or microprocessor, for example. The processor(s) may be a multiprocessor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, the edge device 20 is shown in FIG. 1B as constituting a single entity, but it is to be understood that the edge device 20 may be distributed across multiple devices, such as across multiple servers.

The AoA application 135 may provide various data, notifications, and messages to the plurality of care provider devices 120. The data, notifications, and/or messages may include historical data, real-time medical device data (e.g., provided by the streaming server 114), and notifications that may be pushed to the plurality of care provider devices 120 from the event notification service 112 via the MDD processing system 12 or another a cloud-based service.

As mentioned above and as will be explained in more detail below, the AoA application 135 may be visualized on a care provider device in the form of one or more dashboards of a GUI. When selected, the AoA status dashboard may be populated with real-time anesthesia monitoring parameters, such most-recently determined values for train of four (TOF), state entropy (SE), response entropy (RE), surgical pleth index (SPI), bispectral index (BIS), and so forth, determined from the medical device data 107 obtained from the medical devices. When the medical device data 107 is received by the edge device 20, some or all of the medical device data may be processed by the stream processing module 106 and supplied to the streaming server 114, which may then supply the real-time patient monitoring parameter values to a requesting care provider device. For example, when a user is viewing the AoA status dashboard of the AoA application 135 on the care provider device 134, the graphical user interface may include tiles or other display areas where the most-recently determined values for selected anesthesia monitoring parameters are displayed (for example, as shown in FIG. 2 and explained in more detail below). For example, entropy is a measure of irregularity in any signal. During general anesthesia, electroencephalograph (EEG) and/or electromyograph (EMG) signals change from irregular to more regular patterns when anesthesia deepens. The stream processing module 106 measures these changes by quantifying the irregularity of EEG and EMG signals, which in turn give an indication of the level of consciousness (LOC) of the patient. Alternatively, the stream processing module 106 may determine a BIS value from the EEG signals, which may be further used to determine the LOC. As another example, when neuromuscular blocking agents (NMBAs) are given to block musculoskeletal activity during anesthesia, a nerve stimulator may be used to assess nerve function, and the stream processing module 106 may use TOF monitoring to describe the pattern of electrical nerve stimulation and evaluate the degree of neuromuscular blockade. As still another example, the stream processing module 106 may receive pulse oximetry measurements and derive the SPI value, which may be used to monitor nociceptive stimuli and antinociceptive drug effects during surgery.

The streaming server 114 may stream the most-recently determined values for the selected anesthesia monitoring parameters to the care provider device 134, which may then populate the received values into the graphical user interface. The stream processing module 106 may include rule-based streaming analytics algorithms applying windowing functions (sliding, tumbling, hopping, etc.) used for data analysis and event detection, thereby triggering alerts, detection of surgical phases, triaging algorithms, etc. Furthermore, the stream processing module 106 coupled with inference engine 110 may perform predictions such as continuously predictive scoring, non-compliant case identification, and clinical decision support in general.

The determination of which data to send to which care provider device may be based at least in part on data requests sent by the care provider devices to the edge device 20. The edge device 20 may include a representational state transfer (REST) server, for example, that may receive data requests from the care provider devices 120 and may respond to the data requests by commanding the streaming server 114 to stream selected medical device data to a requesting care provider device(s). The streaming server 114 may maintain a stateful session (e.g., WebSocket) with each client (e.g., the care provider devices). The medical device data may be adapted (transformed and filtered) before being streamed to the client devices.

Figure 3:
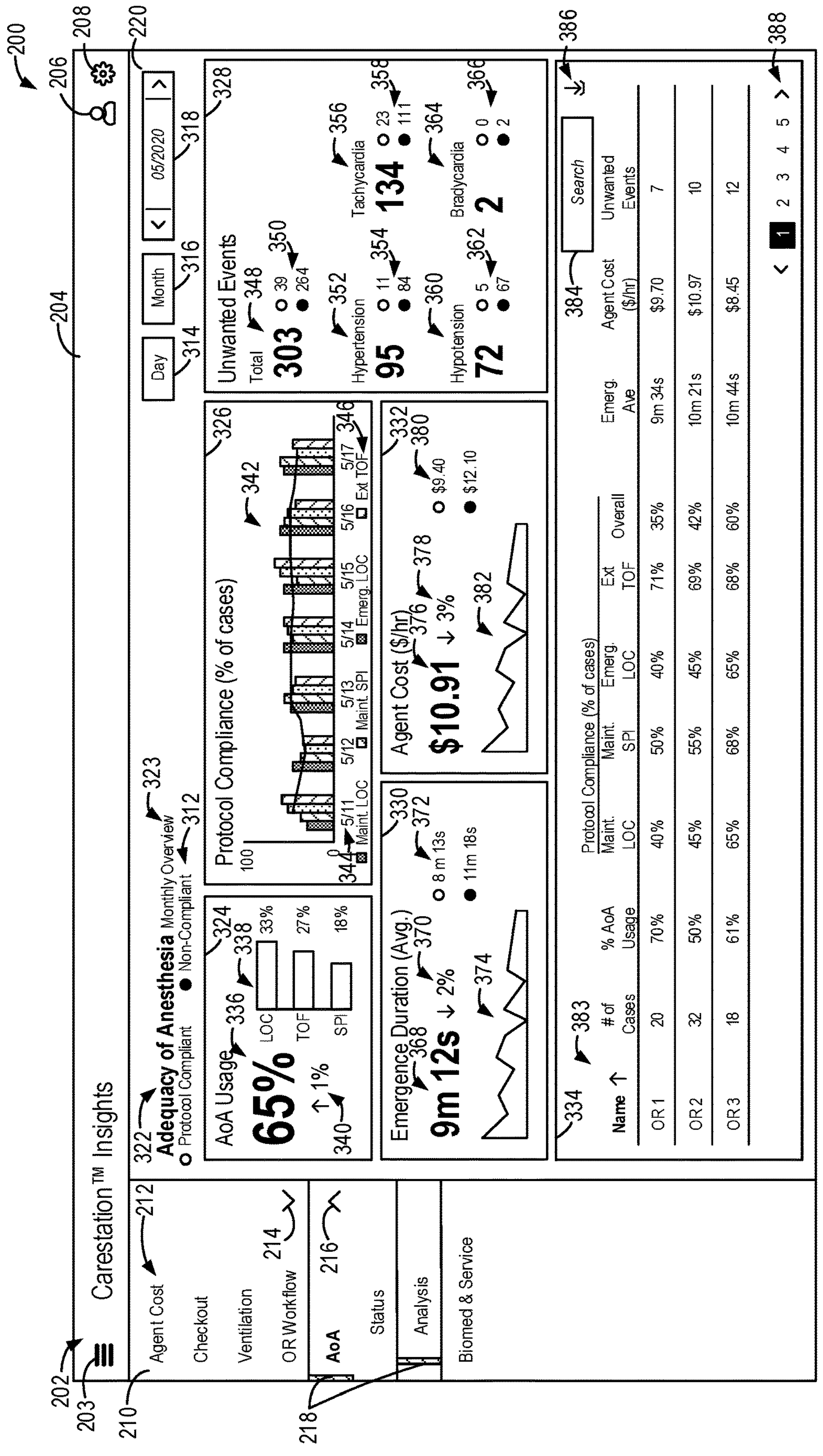
FIG. 3 shows a first exemplary AoA analysis dashboard generated via the AoA application, according to an embodiment.
Figure 4:
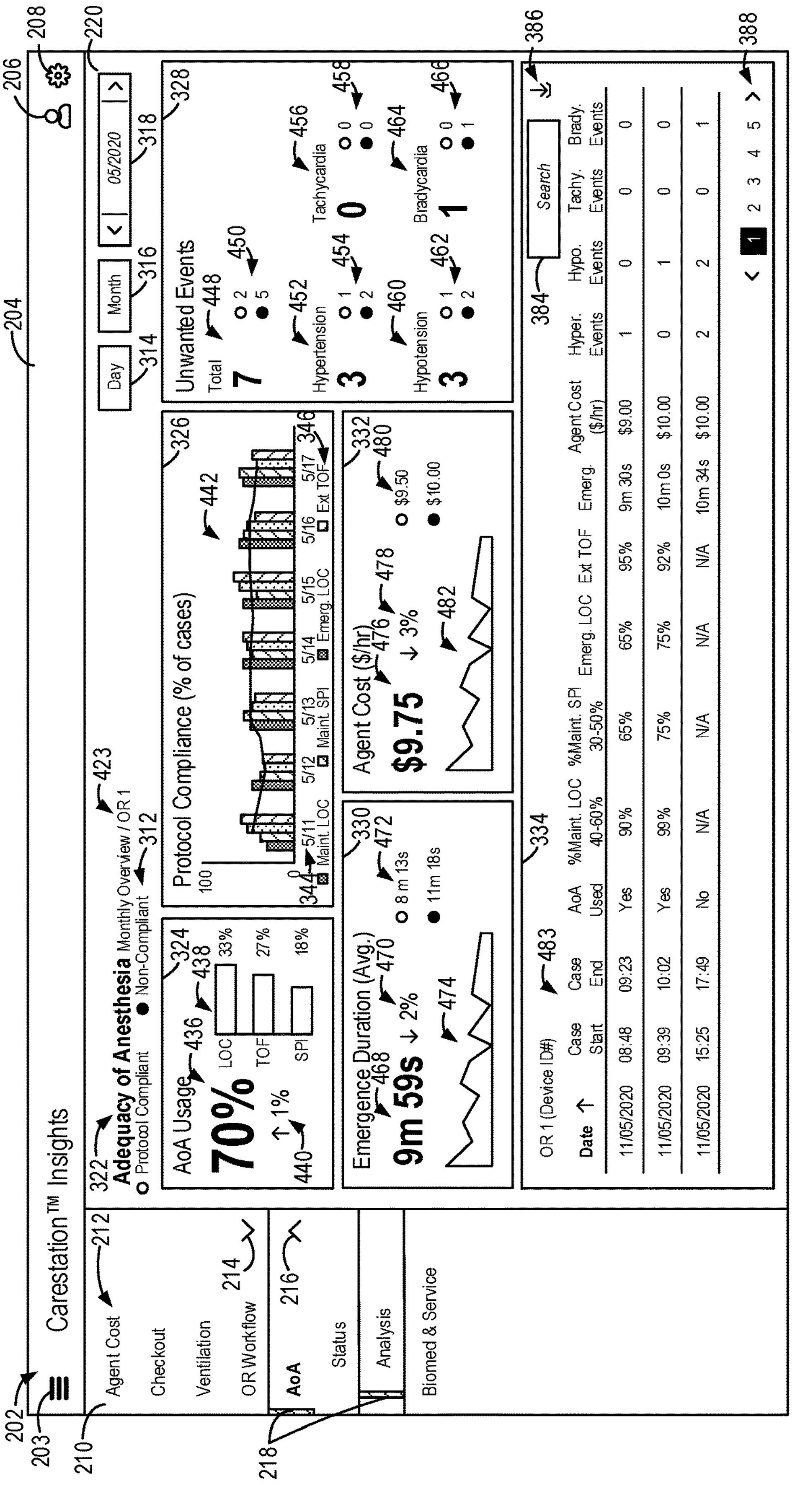
FIG. 4 shows a second exemplary AoA analysis dashboard generated via the AoA application, according to an embodiment.

The data requests from the care provider devices 120 may also include requests for historical data (e.g., prior or non-real-time patient monitoring parameter values). The historical data may include trends of selected anesthesia monitoring parameters over time. For example, as shown in FIGS. 3 and 4 and explained in more detail below, the AoA analysis dashboard be displayed on a care provider device as part of the AoA application 135 that shows values for selected anesthesia monitoring parameters over time as trend lines, graphs, or percentages. The trends may be assembled from stored medical device data (e.g., stored in data storage 104). When a user requests to view the AoA analysis dashboard on a care provider device, the care provider device may send a request for the trends within a selected data range (e.g., operating room(s) and/or date(s)) to the edge device 20, and the edge device 20 may obtain the trends from the data storage 104. Alternatively, the edge device 20 may obtain relevant stored medical device data, and the trends may be assembled at a different location (e.g., by the care provider device).

The AoA application 135 may generate and/or send various notifications based on the medical device data 107 received from the various medical devices. The notifications may include threshold-based notifications, where the notification is generated and output to one or more care provider devices in response to an anesthesia monitoring parameter value meeting a predetermined condition relative to a threshold. For example, a notification be generated and sent to a care provider device in response to an anesthesia monitoring parameter being without a pre-set range for AoA protocol compliance, such as will be shown in FIG. 2 and explained in more detail below.

As mentioned above, the supervisory application 44 is configured to apply insights to the received medical device data in order to provide user-selected notifications of patient status. The insights may include the rule-based streaming analytics algorithms performed by the stream processing module 106 and/or inference engine 110 described above (e.g., event detection, detection of anesthesia phases, etc.). The insights may include artificial intelligence-based models, such as machine learning or deep learning models. In general, any algorithm, model, or set of rules that may be applied to the medical device data 107 in order to monitor patient state may be considered an insight. In some examples, particularly where the insight requires a high amount of processing power, the insight may be stored/executed on a cloud based device such as the MDD processing system 12.

In some examples, an insight may include, as an input, the result of another insight. For example, a first insight may include an algorithm that determines a current anesthesia delivery phase for an anesthesia delivery machine. The output/result of the first insight may be displayed within the AoA status dashboard of the AoA application, when selected, as will be explained in more detail below. The result of the first insight may also be used as input, along with the medical device data, to a second insight. For example, the second insight may include a duration of an emergence phase of the anesthesia delivery (e.g., an emergence duration). The second insight may be used as an input for a third insight, such as an average emergence duration, that is displayed within the AoA analysis dashboard of the AoA application, when selected.

The inference engine 110 may be used with artificial intelligence (AI) based models, such as trained deep learning models, to process the incoming data and derive conclusions (insights) from the facts and rules contained in the various machine learning models. The inference engine 110 may be the run-time engine for AI based algorithms. In addition, there may be a deep learning and/or learning network in the cloud, e.g., the MDD processing system 12, to train algorithms, where very high computing resources are used.

Thus, as explained above, the AoA application 135 may include a backend hosted on the edge device 20, where the backend includes a plurality of micro services, such as the rules engine 108, inference engine 110, event notification service 112, and streaming server 114. The AoA application 135, via the backend/edge device 20, may output real-time medical device data to a plurality of care provider devices, trends of medical device data, messages, notifications/results, and/or other information as requested by the front end of the AoA application 135 that is executed on the care provider devices. The front end of the AoA application 135 may include a visualization platform that may be stored on each care provider device. The visualization platform may render the data received from the edge device 20 into one or more graphical user interfaces. Additionally, the aspects of the AoA application 135 that are saved on each care provider device may include various container, component, and presentation layers to receive the data from the edge device 20, populate the graphical user interface with the received data, send and receive messages, display notifications, collect GUI settings and other requested customizations (and send the settings/configurations to the edge device 20) and so forth. As an example, the historical data received form the edge device 20 (e.g., the trends) may be sent to a first layer via a REST application programming interface (API), the real-time medical device data may be streamed to the first layer via a web socket, and the push notifications sent from the MDD processing system 12 may be received, processed, and displayed via the visualization platform. Further, when interacting with the graphical user interface of the AoA application 135, the user may adjust various settings (such as which anesthesia monitoring parameters to display), activate or deactivate notifications, create insights, and so forth. These user-specific preferences/configurations may be saved on the edge device 20 in a preferences/configuration database.

In some embodiments, medical device data and/or other information requested via the AoA application 135 may be obtained from an electronic medical records (EMR) database 122. For example, historical data (e.g., trends) may be obtained from the EMR database 122 in addition to or instead of the data storage 104. The EMR database 122 may be an external database via a secured hospital interface, or the EMR database 122 may be a local database (e.g., housed on a device of the hospital). The EMR database 122 may be a database stored in a mass storage device configured to communicate with secure channels (e.g., HTTPS and TLS), and store data in encrypted form. Further, the EMR database 122 is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

The edge device 20 may be implemented in a variety of hardware and/or software implementations and it should be noted that such implementations are not considered to be limiting. For example, it is contemplated that any or all of the edge device 20 may be embodied exclusively in hardware, exclusively in software, exclusively in firmware, or in any combination of hardware, software, and/or firmware. The examples provided herein are not the only way to implement such methods and systems.

In exemplary and non-limiting embodiments of the edge device, the edge device 20 is implemented by one or more processors or computing devices. Memory and processors as referred to herein can be standalone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to, RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

FIGS. 2-5 show different dashboards of an example graphical user interface (GUI) 200 of an AoA application. For example, the GUI 200 may be displayed when the AoA application 135 of FIG. 1B is launched on a care provider device. Components of GUI 200 throughout FIGS. 2-5 are numbered the same and will not be re-introduced. The GUI 200 may be displayed on a display device 202. The display device 202 may include a screen on which the GUI is displayed and may be coupled to and/or included as a part of a computing device, such as the care provider device 134 of FIG. 1B. The GUI 200 may be displayed in response to a user request to display the GUI. For example, a user may launch the AoA application 135 by selecting a corresponding icon displayed on a home page of the display device. When the AoA application 135 launches (at least initially), the user may be authenticated via a suitable authentication method, such as via a password, facial recognition, fingerprint recognition, etc.

Upon authentication, the user may select to view a particular dashboard (or window) of the GUI 200 from a menu 212. Referring first to FIG. 2, the menu 212 is located in a sidebar 210 that is adjacent to a parameter display window 220. Within the menu, an "AoA" option and a "status" option, which is located in a drop-down menu 216 of the AoA option, are both selected, as shown by a selection indicator 218. As a result, the parameter display window 220 is populated by an AoA status dashboard 222. Further, the GUI 200 includes a title bar 204, from which the user may select a different application via a selector 203, change users or log out via a user icon 206, or customize display settings via a display icon 208. For example, the user may customize the display so that the sidebar 210 is hidden or located in another position on the display device 202. It may be understood that the particular arrangement of the various information shown in GUI 200 is illustrative, and other arrangements are possible.

The AoA status dashboard 222 includes a case overview section 223 and a case status section 224 as an array of tiles showing real-time patient information. Each tile displays grouped and curated information. For example, the case overview section 223 includes an active case tile 226, a check protocol tile 228, an inducing tile 230, a maintenance tile 232, and an emerging tile 234. The active case tile 226 tabulates a total number of active cases and includes an indication of the number of active cases that are using an AoA protocol. As elaborated herein, the AoA protocol includes pre-set ranges for different anesthesia monitoring parameters, and when the AoA protocol is used, a computing device (e.g., the edge device 20 of FIGS. 1A and 1B) may determine whether a particular clinical case is in compliance with the protocol. The number of cases using the AoA protocol is indicated via an AoA icon 236. In the illustrative example shown in FIG. 2, 9 out of 12 total active cases are using the AoA protocol. The check protocol tile 228 tabulates the number of cases using the AoA protocol that are non-compliant with the AoA protocol, as shown by a non-compliance alert 238. In the illustrative example shown in FIG. 2, the check protocol tile 228 indicates that 2 of the 9 cases using the AoA protocol, as shown in the active case tile 226, are non-compliant with the AoA protocol. Thus, the non-compliance alert 238 may be generated and displayed in response to the number of cases using the AoA protocol that are non-compliant with the AoA protocol being greater than zero. The inducing tile 230 tabulates the number of patients that are currently in an induction phase of the anesthesia, including the total number versus the number using the AoA protocol, as indicated by the AoA icon 236. Similarly, the maintenance tile 232 tabulates the number of patients that are currently in a maintenance phase of the anesthesia, including the total number versus the number using the AoA protocol. The emerging tile 234 tabulates the number of patients that are currently in an emergence phase of the anesthesia, including the total number versus the number using the AoA protocol. Thus, the case overview section 223 provides a high-level overview of the current case status and gives an indication of AoA non-compliance, but does not indicate which operating rooms are using the AoA protocol, which have non-compliant cases, or which parameters are non-compliant.

The case status section 224 includes individual status overview tiles for each operating room, including an operating room (OR) 1 status tile 240, an OR 2 status tile 242, an OR 3 status tile 244, an OR 4 status tile 246, an OR 5 status tile 248, an OR 6 status tile 250, an OR 7 status tile 252, an OR 8 status tile 254, an OR 9 status tile 256, an OR 10 status tile 258, an OR 11 status tile 260, and an OR 12 status tile 262. Operating rooms having active cases using the AoA protocol include the AoA icon 236 within the tile, whereas the operating rooms that are not using the AoA protocol do not include the AoA icon 236. Further, the operating rooms that are not using the AoA protocol may include limited patient monitoring parameters compared with those that are using the AoA protocol. In the example shown, OR 1, OR 2, OR 3, OR 5, OR 6, OR 7, OR 8, and OR 9 have active cases using the AoA protocol (e.g., the 9 active cases shown next to the AoA icon 236 in the active case tile 226), whereas OR 10, OR 11, and OR 12 have active cases that are not using the AoA protocol (e.g., the cases of the 12 total active cases shown in the active case tile 226).

Various information shown in each operating room status tile will now be described with respect to the OR 1 status tile 240 for simplicity, although it may be understood that each operating room status tile may include similar information. The OR 1 status tile 240 includes an identifier 264, which states the name or other identifying information for the particular operating room (e.g., OR 1), patient monitoring parameters 266, and an anesthesia phase indicator 268. The anesthesia phase indicator 268 includes an induction phase icon 270, a maintenance phase icon 272, and an emergence phase icon 274. The current phase of the anesthesia is indicated by highlighting, coloring, or otherwise differently displaying the icon corresponding to the current phase of anesthesia. For example, the emergence phase icon 274 is differently filled than the induction phase icon 270 and the maintenance phase icon 272 within the OR 1 status tile 240, indicating that the patient in OR 1 is in the emergence phase. Further, a duration of the emergence phase is indicated adjacent to the emergence phase icon 274, indicating that the patient has been in the emergence phase for 5 minutes and 13 seconds in the present illustrative example.

The patient monitoring parameters 266 include a TOF percentage, an indication of the LOC (which may be provided via SE/RE values or BIS, depending on which is used), and the SPI. Because the values given for each of the patient monitoring parameters 266 in the OR 1 status tile 240 do not include the non-compliance alert 238, it may be understood that the clinical case in OR 1 is compliant with the AoA protocol. In contrast, the SE/RE values within the OR 2 status tile 242 include the non-compliance alert 238, indicating that the clinical case in OR 2 is non-compliant. Further, the SPI value in the OR 8 status tile 254 also includes the non-compliance alert 238, indicating the clinical case in OR 8 is also non-compliant with the AoA protocol. As such, the case status section 224 provides a breakdown of the ongoing clinical cases and allows the user to easily observe which clinical case(s) and which aspects of the clinical case(s) are non-compliant with the pre-set AoA protocol. For example, the user may choose to provide feedback to the clinicians in operating rooms 2 and 8.

Further, values for the patient monitoring parameters 266 are not shown for the operating rooms that are not using the AoA protocol. For example, selecting usage of the AoA protocol may trigger the analysis of the medical device data, and so the medical device data may not be analyzed for the patient monitoring parameters 266 that give an indication of the AoA protocol compliance or non-compliance when the AoA protocol is not selected at the operating room.

Further, the user may use a phase selection drop-down menu 276 and/or a status selection drop-down menu 278 to filter the information shown in the case status section 224, as desired. For example, the user may select the emergence phase within the phase selection drop-down menu 276. In the present example, selecting the emergence phase would result in only the OR 1 status tile 240 and the OR 3 status tile 244 being displayed.

FIGS. 3 and 4 show the GUI 200 with an "analysis" option selected within the drop-down menu 216 of the AoA option of the menu 212, as indicated via the selection indicator 218. As such, an AoA analysis dashboard 322 is shown within the parameter display window 220 in each of FIGS. 3 and 4.

The AoA analysis dashboard 322 includes an AoA usage tile 324, a protocol compliance tile 326, an unwanted events tile 328, an emergence duration tile 330, an agent cost tile 332, and a data summary tile 334. Further, a legend 312 shows that data values corresponding to AoA protocol compliant cases are indicated by a first symbol type (e.g., an open circle) and that data values corresponding to AoA protocol non-compliant cases are indicated by a second symbol type (e.g., a filled circle in the present example). Further, a day input 314, a month input 316, and a calendar selection input 318 enable the user to select different date ranges from which data will be shown. In the example shown, data for May of 2020 (e.g., 05/2020) is selected to be shown via the AoA analysis dashboard 322.

Each tile within the AoA analysis dashboard 322 may be configured to display different information depending on a selected data range. Referring first to FIG. 3, the AoA analysis dashboard 322 shows a global monthly overview 323 for the selected date range. However, daily, weekly, or yearly global overviews are also possible. Thus, the AoA usage tile 324 shows a global AoA usage percentage 336, a global AoA usage trend 340, and global protocol usage percentages 338 for each of LOC, SPI, and TOF. The global AoA usage percentage 336 indicates a percentage of the total cases performed during the specified date range that used the AoA protocol, and the global AoA usage trend 340 indicates a change in the usage percentage compared to a previous data period. For example, when the global monthly overview 323 is shown, the global AoA usage trend 340 compares the data for the currently shown month with the previous month or number of months. As used herein, the term "global" is meant to denote data acquired from every operating room within a healthcare facility and/or monitored using the AoA application, such as in contrast to data from one or more selected operating rooms, such as will be elaborated with respect to FIG. 4.

The protocol compliance tile 326 provides an indication of the number of cases complying with each parameter of the AoA protocol for the selected date range. For example, the protocol compliance tile 326 includes global protocol compliance graphic 342, which includes a bar graph indicating protocol compliance for each day 344 within the selected date range for each of a maintenance LOC parameter of the AoA protocol, a maintenance SPI parameter of the AoA protocol, an emergence LOC parameter of the AoA protocol, and an extubation TOF parameter of the AoA protocol, as indicated by a legend 346. Further, the global protocol compliance graphic 342 includes a trendline.

The unwanted events tile 328 provides a monthly global total number of unwanted events 348 as well as a compliance indicator 350 that subdivides the monthly global total number of unwanted events into those occurring during cases that were in compliance with the AoA protocol versus those that were not in compliance with the AoA protocol, such as according to the legend 312. The unwanted events tile 328 further subdivides the monthly global total number of unwanted events 348 according to the type of unwanted event. For example, the unwanted events tile 328 shows a monthly global total of hypertension events 352 along with a corresponding compliance indicator 354 for the hypertension events, a monthly global total of tachycardia events 356 along with a corresponding compliance indicator 358 for the tachycardia events, a monthly global total of hypotension events 360 along with a corresponding compliance indicator 362 for the hypotension events, and a monthly global total of bradycardia events 364 along with a corresponding compliance indicator 366 for the bradycardia events. Settings for detecting the unwanted events will be discussed below with respect to FIGS. 5 and 7.

The emergence duration tile 330 shows a global average emergence duration 368 for the selected date range as well as an emergence duration trend 370, a compliance indicator 372, and an emergence duration graphic 374. The emergence duration trend 370 indicates a percentage change in the global average emergence duration 368 compared with the previous data period. In the example shown in FIG. 3, the emergence duration trend 370 shows that the global average emergence duration has decreased by 2%. Further, the compliance indicator 372 subdivides the global average emergence duration 368 into a global average emergence duration for cases that were protocol compliant versus non-compliant, as indicated by the legend 312. The emergence duration graphic 374 shows how the emergence duration average varies over time throughout the selected data range.

The agent cost tile 332 shows a global average agent cost (e.g., in dollars per hour) 376 for the selected date range as well as an agent cost trend 378, a compliance indicator 380, and an agent cost graphic 382. The agent cost trend 378 indicates a percentage change in the global average agent cost 376 compared with the previous data period. In the example shown in FIG. 3, the agent cost trend 378 shows that the global average agent cost has decreased by 3%. Further, the compliance indicator 380 subdivides the global average agent cost 376 into a global average agent cost for cases that were protocol compliant versus non-compliant, as indicated by the legend 312. The agent cost graphic 382 shows how the agent cost varies over time throughout the selected data range.

The data summary tile 334 includes a monthly global summary table 383 that shows sortable and searchable data for each operating room. For example, the monthly global summary table 383 may be searchable via a search function 384 and may be downloadable via user selection of a download icon 386. Further, only a portion of the monthly global summary table 383 may be displayed within the data summary tile 334 due to an amount of information included in the monthly global summary table 383, and thus, the user may use a page selector 388 to navigate to different portions of the monthly global summary table 383.

Each row of the monthly global summary table 383 corresponds to data from a different operating room (e.g., OR 1, OR 2, OR 3, etc.). In the example illustrated in FIG. 3, each column of the monthly global summary table 383 includes data relating to AoA protocol usage, compliance, and analysis, such as the number of cases performed in the corresponding operating room, the percentage of those cases that used the AoA protocol, and the percentage of the cases using the AoA protocol that were compliant with each parameter of the AoA protocol. The columns of the monthly global summary table 383 further delineate the average emergence duration of cases performed in the corresponding operating room, the agent cost per hour of the cases performed in the corresponding operating room, and the number of unwanted events in that operating room. It may be understood that other data relating to AoA protocol usage, compliance, and analysis may additionally or alternatively be shown within the monthly global summary table 383.

As mentioned above, each tile within the AoA analysis dashboard 322 may be display different information depending on a selected data range. Turning now to FIG. 4, an individual operating room monthly overview 423 is provided in the AoA analysis dashboard 322. For example, the user may select a single operating room by clicking a link to that operating room. Aspects of the AoA analysis dashboard 322, such as the tiles shown within the dashboard, are numbered the same as in FIG. 3 and will not be reintroduced. As such, only differences in the values and information displayed in the operating room monthly overview 423 compared with the global monthly overview 323 will be discussed below. Further, although a monthly overview for operating room 1 is shown, weekly, or yearly global overviews are also possible and for other operating rooms.

In the example shown in FIG. 4, the AoA usage tile 324 shows an OR 1-specific AoA usage percentage 436, an OR 1-specific AoA usage trend 440, and OR 1-specific protocol usage percentages 438 for each of LOC, SPI, and TOF. The OR 1-specific AoA usage percentage 436 indicates a percentage of the total cases performed in operating 1 during the specified date range that used the AoA protocol, and the OR 1-specific AoA usage trend 440 indicates a change in the usage percentage compared to a previous data period. For example, when the individual operating room monthly overview 423 is shown, the OR 1-specific AoA usage trend 440 compares the data for the currently shown month with the previous month or number of months. As used herein, the term "OR 1-specific" is meant to denote data acquired only from operating room 1, in contrast to data from every operating room of the facility, such as described with respect to FIG. 3.

The protocol compliance tile 326 provides an indication of the number of cases performed within operating room 1 that were in compliance with each parameter of the AoA protocol for the selected date range. For example, the protocol compliance tile 326 includes OR 1-specific protocol compliance graphic 442, which includes a bar graph indicating protocol compliance for each day 344 within the selected date range for each of parameter of the AoA protocol, such as mentioned above with respect to FIG. 3. Further, the OR 1-specific protocol compliance graphic 442 includes a trendline.

The unwanted events tile 328 provides a monthly OR 1-specific total number of unwanted events 448 as well as a compliance indicator 450 that subdivides the monthly OR 1-specific total number of unwanted events into those occurring during cases that were in compliance with the AoA protocol versus those that were not in compliance with the AoA protocol, such as according to the legend 312. The unwanted events tile 328 further subdivides the monthly OR 1-specific total number of unwanted events 448 according to the type of unwanted event. For example, the unwanted events tile 328 shows a monthly OR 1-specific total of hypertension events 452 along with a corresponding compliance indicator 454 for the hypertension events, a monthly OR 1-specific total of tachycardia events 456 along with a corresponding compliance indicator 458 for the tachycardia events, a monthly OR 1-specific total of hypotension events 460 along with a corresponding compliance indicator 462 for the hypotension events, and a monthly OR 1-specific total of bradycardia events 464 along with a corresponding compliance indicator 466 for the bradycardia events.

The emergence duration tile 330 shows an OR 1-specific average emergence duration 468 for the selected date range as well as an emergence duration trend 470, a compliance indicator 472, and an emergence duration graphic 474. The emergence duration trend 470 indicates a percentage change in the OR 1-specific average emergence duration 468 compared with the previous data period. In the example shown in FIG. 4, the emergence duration trend 470 shows that the OR 1-specific average emergence duration has decreased by 2%. Further, the compliance indicator 472 subdivides the OR 1-specific average emergence duration 468 into an OR 1-specific average emergence duration for cases that were protocol compliant versus non-compliant, as indicated by the legend 312. The emergence duration graphic 374 shows how the emergence duration average varies over time throughout the selected data range for operating room 1.

The agent cost tile 332 shows an OR 1-specific average agent cost 476 for the selected date range as well as an agent cost trend 478, a compliance indicator 480, and an agent cost graphic 482. The agent cost trend 478 indicates a percentage change in the OR 1-specific average agent cost 476 compared with the previous data period. In the example shown in FIG. 4, the agent cost trend 478 shows that the OR 1-specific average agent cost has decreased by 3%. Further, the compliance indicator 480 subdivides the OR 1-specific average agent cost 476 into an OR 1-specific average agent cost for cases that were protocol compliant versus non-compliant, as indicated by the legend 312. The agent cost graphic 482 shows how the agent cost varies over time throughout the selected data range.

The data summary tile 334 includes a monthly OR 1-specific summary table 483 that shows sortable and searchable data for each case within the date range for operating room 1. For example, the monthly OR 1-specific summary table 483 may be searchable via the search function 384. Further, only a portion of the monthly OR 1-specific summary table 483 may be displayed within the data summary tile 334 due to an amount of information included in the monthly OR 1-specific summary table 483, and thus, the user may use the page selector 388 to navigate to different portions of the monthly OR 1-specific summary table 483.

Each row of the monthly OR 1-specific summary table 483 corresponds to data from a different clinical case. In the example illustrated in FIG. 4, each column of the monthly OR 1-specific summary table 483 includes data relating to case timing (e.g., case start and case end), AoA protocol usage, AoA protocol compliance for each parameter of the AoA protocol, and analysis (e.g., emergence duration, agent cost, and a number of each type of unwanted event). It may be understood that other data relating to AoA protocol usage, compliance, and analysis may additionally or alternatively be shown within the monthly OR 1-specific summary table 483.

Next, FIG. 5 shows an AoA administration dashboard 522 of the GUI 200. For example, the user may select an "AoA configuration" option, as shown by the selection indicator 218, in order to program or adjust one or more parameters of the AoA protocol. The AoA administration dashboard 522 includes a protocol compliance section 514 and an unwanted events section 516.

Via the protocol compliance section 514 of the AoA administration dashboard 522, the user may set thresholds for each parameter of the AoA protocol that dictate which clinical cases are compliant versus those that are non-compliant. The protocol compliance section 514 includes a key 524 that defines acronyms used within the protocol compliance section 514 (e.g., LOC is level of consciousness, SE is state entropy, BIS is bispectral index, TOF is train of four, and SPI is surgical pleth index) and a plurality of inputs for selecting lower or upper bounds for each parameter of the AoA protocol. The parameters of the AoA protocol include a maintenance stage LOC, an emergence stage LOC, an extubation TOF, and a maintenance phase SPI.

For the maintenance phase LOC, the user may select a lower maintenance phase LOC threshold (or bound) via an input 526, an upper maintenance phase LOC threshold (or bound) via an input 528, and an in range maintenance phase LOC qualifier via an input 530. For example, the lower maintenance phase LOC threshold and the upper maintenance phase LOC threshold may define a range of desired maintenance phase LOC values for performing anesthesia. For example, whether determined via SE or BIS, the range of desired maintenance phase LOC values may be set ensure that the anesthesia is not so deep to cause hemodynamic changes but not so light that the patient may gain recall or awareness. Further, maintenance phase LOC values that are below the lower maintenance phase LOC threshold or above the upper maintenance phase LOC threshold are non-compliant with the AoA protocol. Further, because the LOC may fluctuate during the anesthesia, the in range maintenance phase LOC qualifier defines the percentage of the total maintenance phase duration for the maintenance phase LOC to be between the lower maintenance phase LOC threshold and the upper maintenance phase LOC threshold and qualify as compliant. Using the values shown in FIG. 5 as an illustrative example, the maintenance phase LOC AoA protocol parameter is set such that a clinical case having maintenance phase LOC values between 40% and 60% for at least 90% of the total maintenance phase duration will be considered protocol compliant, whereas a clinical case having maintenance phase LOC values between 40% and 60% for less than 90% of the total maintenance phase duration will not be considered protocol compliant.

For the emergence phase LOC, the user may select a lower maintenance phase LOC threshold (or bound) via an input 532. Because the LOC is meant to increase during the emergence phase, the emergence phase LOC does not include an upper threshold. Thus, whether determined via SE or BIS, the range of desired emergence phase LOC values may be set to reduce an emergence duration. Using the value shown in FIG. 5 as an illustrative example, the emergence phase LOC AoA protocol parameter is set such that a clinical case having emergence phase LOC values that are at least 60% is considered protocol compliant, whereas a clinical case having emergence phase LOC values less than 60% is not considered to be protocol compliant.

For the extubation TOF, the user may select a lower extubation TOF threshold (or bound) via an input 534. Because the extubation is performed during the end of the anesthetic procedure, the extubation TOF does not include an upper threshold. For example, the lower extubation TOF threshold may be set to reduce an emergence duration. Using the value shown in FIG. 5 as an illustrative example, the extubation TOF AoA protocol parameter is set such that a clinical case having extubation TOF values of at least 90% is considered protocol compliant, whereas a clinical case having extubation TOF values less than 90% is not considered to be protocol compliant.

For the maintenance phase SPI, the user may select a lower maintenance phase SPI threshold (or bound) via an input 536, an upper maintenance phase SPI threshold (or bound) via an input 538, and an in range maintenance phase SPI qualifier via an input 540. For example, the lower maintenance phase SPI threshold and the upper maintenance phase SPI threshold may define a range of desired maintenance phase SPI values for performing anesthesia. For example, the range of desired maintenance phase SPI values may guide analgesia to reduce usage of noradrenaline and opioids. Further, maintenance phase SPI values that are below the lower maintenance phase SPI threshold or above the upper maintenance phase SPI threshold are non-compliant with the AoA protocol. Further, because the SPI may fluctuate during the anesthesia, the in range maintenance phase SPI qualifier defines the percentage of the total maintenance phase duration for the maintenance phase SPI to be between the lower maintenance phase SPI threshold and the upper maintenance phase SPI threshold and qualify as compliant. Using the values shown in FIG. 5 as an illustrative example, the maintenance phase SPI AoA protocol parameter is set such that a clinical case having maintenance phase SPI values between 20% and 50% for at least 90% of the total maintenance phase duration will be considered protocol compliant, whereas a clinical case having maintenance phase SPI values between 20% and 50% for less than 90% of the total maintenance phase duration will not be considered protocol compliant.

The unwanted events section 516 allows the user to define desired ranges for blood pressure and heart rate values via a plurality of inputs. The unwanted events section 516 includes a key 542 that defines acronyms used within the unwanted events section 516 (e.g., MAP stands for mean arterial pressure, ECG corresponds to electrocardiogram). The user may set a lower blood pressure threshold (or bound) via an input 544, an upper blood pressure threshold (or bound) via an input 546, a lower heart rate threshold (or bound) via an input 548, and an upper heart rate threshold (or bound) via an input 550. For example, the lower blood pressure threshold and the upper blood pressure threshold may define the desired range for the blood pressure, and blood pressures outside of the desired range (e.g., below the lower blood pressure threshold or above the upper blood pressure threshold) correspond to unwanted events. Similarly, the lower heart rate threshold and the upper heart rate threshold may define the desired range for the heart rate, and heart rates outside of the desired range (e.g., below the lower heart rate threshold or above the upper heart rate threshold) correspond to unwanted events.

Further, each unwanted event may be classified as a particular type of unwanted event based on its relation to the corresponding thresholds. For example, the event may be classified as hypertension in response to the blood pressure being greater than the upper threshold blood pressure or hypotension in response to the blood pressure being less than the lower threshold blood pressure. Similarly, the event may be classified as tachycardia in response to the heart rate being greater than the upper threshold heart rate or bradycardia in response to the heart rate being less than the lower threshold heart rate.

Thus, the AoA administration dashboard 522 of the AoA application, as accessed via the GUI 200, enables a qualified user (e.g., a supervising care provider) to configure settings for each parameter of the AoA protocol that define protocol compliance versus non-compliance as well as settings for detecting unwanted events. As such, the AoA protocol may help clinicians maintain sufficient anesthesia for performing patient procedures while reducing unwanted events and other complications. Further, the AoA protocol may help decrease anesthetic agent usage by helping optimize the anesthesia amount given to each patient and, thus, may help decrease an amount of money spent on the anesthetic agent. Further, the AoA application may allow the user to oversee multiple patients at one time, from any location within a medical facility. The AoA application may present patient monitoring parameters in real-time, such as via the AoA status dashboard 222 of FIG. 2, as well as historical data such as changes in anesthesia parameters over time, such as via the AoA analysis dashboard 322 of FIGS. 2 and 3, as explained above.

FIGS. 6A and 6B show a flow chart illustrating an example method 600 for using an AoA application to generate and display AoA parameters and analysis via a corresponding dashboard on a user interface. The AoA application, and thus the method 600, may be implemented by one or more computing devices, such as a care provider device (e.g., care provider device 134 of FIG. 1B) used in combination with an edge device connected to the care provider device (e.g., edge device 20), a cloud in communication with the edge device and/or care provider device (e.g., MDD processing system 12), or any appropriate combination thereof.

At 602, the method 600 includes receiving medical device data from a plurality of medical devices. The medical device data may be received from one or more medical devices, such as the medical devices 16 of FIG. 1A, during anesthesia delivery to one or more patients. The medical device data may be received by a data ingestion module of the edge device, for example, and in some examples may be processed by a stream processing module of the edge device, as explained above with respect to FIG. 1B. Additionally or alternatively, the medical device data may be sent to a cloud-based device, such as the MDD processing system 12 of FIG. 1A, where the medical device data may be ingested by an ingestion module (e.g., high speed ingestion module 22). As also discussed above, the medical device data comprises both patient monitoring data and anesthesia delivery machine data.

At 604, the method 600 includes analyzing the medical device data to determine neuromuscular transmission (NMT), SPI, BIS, SE/RE, TOF, and/or LOC values and storing the values in a database. For example, the AoA application may identify individual clinical cases within the medical device data and separately analyze the medical device data for each clinical case. The NMT monitoring may include quantitative monitoring of the NMT blockade during intubation, such as via EMG measurements, whereas SPI may be used to monitor nociceptive stimuli and antinociceptive drug effects using pulse photoplethysmographic data derived from pulse oximetry measurements. The NMT values may be further used to determine TOF values. SE/RE may be determined based on EEG measurements, for example, and may be used to determine a depth of the anesthesia (e.g., the level of consciousness, or LOC). In some examples, BIS monitoring may be used in place of SE/RE to determine the LOC values. Further, the NMT, SPI, BIS, SE/RE (or BIS), TOF, and/or LOC values may be stored, at least temporarily, as data values, trend graphs (which may be a line graphs, a series of bar graphs, or another suitable representation of data values over time) in a data storage location, such as data storage 104 of FIG. 1B and/or operational case database 30 of FIG. 1A.

The medical device data may include real-time medical device data and/or historical (e.g., previously acquired) medical device data, depending on a selection from a user. When historical medical device data is used, the user may further select a data range. For example, the data range may specify a date range for the medical device data and/or one or more operating room(s) where the medical device data was acquired.

At 606, the method 600 includes determining an induction phase, a maintenance phase, and an emergence phase of each clinical case based on the medical device data. For example, the induction phase, the maintenance phase, and the emergence phase comprise different phases of anesthesia, and so the AoA application may distinguish patient monitoring data obtained during each phase based on anesthesia delivery machine data. For example, the AoA application may calculate a flow rate of gases delivered at each time point of a given clinical case to determine the phase of anesthesia. As an example, the flow rate may be a higher value (e.g., greater than a threshold flow rate) during the induction phase, and so a transition to a lower flow rate value (e.g., less than the threshold flow rate) may indicate a maintenance event. A first occurrence of a maintenance event (e.g., earliest with respect to time) from the beginning of agent delivery is considered to be a start of the maintenance phase. As another example, an agent end event may be detected in response to an agent concentration setting transitioning from a non-zero value to zero. If the agent concentration is not increased from zero within three minutes of the agent end event, the agent end event is considered to be the beginning of the emergence phase. The end of the emergence phase is determined in response to a standby flag event within the anesthesia delivery machine data.

Thus, based on these changes in settings to the anesthesia delivery machine, as detected based on the anesthesia delivery machine data, the AoA application may determine the anesthesia phase associated with the time-aligned patient monitoring data. For example, the AoA application may sort or tag the patient monitoring data within the database according to the determined anesthesia phase. Further the AoA application may determine a duration of each of the induction phase, the maintenance phase, and the emergence phase and store the corresponding durations in the database.

Further, extubation time may be determined from the anesthesia delivery machine data. Whenever an end-tidal carbon dioxide (EtCO2) value goes below a lower threshold EtCO2 value (e.g., 0.2) from a higher value for two breaths, it may be determined that a patient disconnected event has occurred. The final (e.g., last with respect to time) occurrence of the patient disconnected event from case start to case end of a given clinical case is considered to be the extubation time.

At 608, the method 600 includes determining an AoA usage percentage based on usage of NMT, SPI, BIS, and/or SE/RE and storing the determined AoA usage percentage in a database. For every clinical case, there are three opportunities to use an AoA protocol by using one or more of NMT, SPI, and SE/RE (or BIS). As such, identifying the use of one or more of NMT, SPI, and SE/RE (or BIS) for a clinical case indicates usage of the AoA protocol for that case. The AoA usage percentage may then be determined as the percentage of cases using the AoA protocol out of a total number of cases. When real-time medical device data is analyzed, the total number of cases may include a total number of currently active cases. When historical medical device data is analyzed, the total number of cases may include all of the clinical cases performed within the selected data range.

At 610, the method 600 includes determining an AoA usage trend and storing the determined usage trend in the database. The AoA usage trend may include a percentage increase or decrease in the AoA usage percentage compared to a previous data range. The previous data range may comprise a previous day, month, or year, depending on selections received from the user via the user interface.

At 612, the method 600 includes determining usage percentages for LOC, NMT, and SPI based on values from the medical device data and storing the determined usage percentages in the database. For example, with the usage of NMT, SPI, BIS, and/or SE/RE identified, a percentage of cases where LOC monitoring (e.g., via SE/RE or BIS) was used out of the total number of cases may be represented by the LOC usage percentage, a percentage of cases where NMT monitoring was used out of the total number of cases may be represented by the NMT usage percentage, and a percentage of cases where SPI monitoring was used out of the total number of cases may be represented by the SPI usage percentage. Thus, the AoA application may not only tabulate AoA protocol usage, but also the usage of individual elements within the AoA protocol.

At 614, the method 600 includes determining protocol compliance percentages based on the medical device data and received AoA protocol selections and storing the determined percentages in the database. As described above with respect to FIG. 5, the AoA application may receive compliance parameters (e.g., thresholds) for each of a maintenance phase LOC, an emergence phase LOC, a maintenance phase SPI, and a extubation TOF. Receiving the AoA protocol selections will be described with respect to FIG. 7 and is also described above with respect to FIG. 5. The AoA application may compare maintenance phase LOC, emergence phase LOC, maintenance phase SPI, and extubation TOF values for a given clinical case to respective parameters for the maintenance phase LOC, the emergence phase LOC, the maintenance phase SPI, and the extubation TOF, as configured by the user, to determine whether or not the clinical case is compliant with each aspect of the AoA protocol. When a clinical case follows desired protocols for each of the maintenance phase LOC, the emergence phase LOC, the maintenance phase SPI, and the extubation TOF, as defined by the respective thresholds, the case is considered to be compliant. When the clinical case does not follow the desired protocol for at least one of the maintenance phase LOC, the emergence phase LOC, the maintenance phase SPI, and the extubation TOF, the case is considered to be non-compliant.

As an example, the TOF % of 5 valid samples acquired prior to the extubation phase may be determined from the patient monitoring data, and the median value calculated. If the median value is greater than a lower extubation threshold, then the case is considered to follow, and be compliant with, the extubation TOF protocol aspect. In contrast, if the median value is less than the lower extubation threshold, then the case is considered to be non-compliant with the extubation TOF protocol aspect and the overall AoA protocol. Thus, the AoA application may determine an overall AoA protocol compliance percentage as well as individual compliance percentages for each of the maintenance phase LOC, the emergence phase LOC, the maintenance phase SPI, and the extubation TOF.

At 616, the method 600 includes determining unwanted intraoperative events based on the medical device data and the received protocol selections and storing an indication of the determined unwanted events in the database. The unwanted intraoperative events may be calculated based on blood pressure and ECG data within the patient monitoring data. A hypertension event is detected in response to the blood pressure increasing above a user-configured upper threshold blood pressure (e.g., as configured via the method of FIG. 7) for a threshold duration (e.g., two consecutive breaths). A hypotension event is detected in response to the blood pressure decreasing below a user-configured lower threshold blood pressure for the threshold duration. A tachycardia event is detected in response to the heart rate increasing above a user-configured upper threshold heart rate for the threshold duration, and a bradycardia event is detected in response to the heart rate decreasing below a user-configured lower heart rate threshold for the threshold duration. Further, the unwanted events may be classified on the basis of the AoA protocol compliance of that particular clinical case.

At 618, the method 600 includes determining an agent cost based on the medical device data and storing the determined agent cost in the database. The cost of agent used may be calculated from the agent consumption data received as part of the anesthesia delivery machine data and a pre-determined agent cost per unit (e.g., per milliliter). This is then divided by the duration of agent use (e.g., in hours) for a given clinical case to arrive at the agent cost per hour. The AoA application may further determine an agent cost trend as a percentage increase or decrease from a previous data range (e.g., a previous day, week, month, year, or different operating room) to provide insights on the variation in agent cost per hour.

At 620 (see FIG. 6B), the method 600 includes, when requested, outputting data values and/or trend graphs for a selected operating room and/or date range for any or all of the AoA usage percentage, as optionally indicated at 622; the AoA usage trend, as optionally indicated at 624; the LOC, NMT, and SPI usage percentages, as optionally indicated at 626; the protocol compliance percentages for the maintenance phase LOC, the emergence phase LOC, the maintenance phase SPI, and the extubation TOF, as optionally indicated at 628; unwanted intraoperative events, as optionally indicated at 630; the emergence duration, as optionally indicated at 632; and the agent cost, as optionally indicated at 634. For example, upon receiving a request from the user to display an AoA analysis dashboard (e.g., the AoA analysis dashboard 322 shown in FIGS. 3 and 4), the AoA application may access values stored in the database to generate trend graphs or other graphic indicators, which may be output to a display device (e.g., the display device 202 of FIGS. 2-5). For example, the protocol compliance percentages for each of the maintenance phase LOC, the emergence phase LOC, the maintenance phase SPI, and the extubation TOF may be represented as a bar chart, such as the global protocol compliance graphic 342 shown in FIG. 3 or operating room-specific protocol compliance graphic 442 shown in FIG. 4. Other examples of the various visual representations of the data are described in detail with respect to FIGS. 2-4.

At 636, the method 600 includes, when requested, outputting real-time anesthesia monitoring parameters, as determined based on the real-time medical device data. For example, the AoA application may analyze the medical device data in real-time, as it is acquired, to determine the real-time TOF %, SE/RE or BIS, and SPI values as well as the current phase of anesthesia, such as described above. The values may be determined simultaneously for one or more active cases. Upon receiving a request from the user to display an AoA status dashboard (e.g., the AoA status dashboard 222 shown in FIG. 2), the AoA application generate an organized layout of the real-time data, which may be output to the display device. For example, the real-time data may be organized according to hospital room, anesthesia phase, etc., and may include data value and graphics/icons, such as described above with respect to FIG. 2.

Outputting the real-time anesthesia monitoring parameters further includes determining protocol non-compliance based on the real-time anesthesia monitoring parameters and the AoA protocol selections, as indicated at 638, and outputting a non-compliance alert in response to the protocol non-compliance, as indicated at 640. For example, the protocol non-compliance may be determined by comparing the real-time extubation TOF, maintenance phase LOC, emergence phase LOC, and maintenance phase SPI values to the respective thresholds described above (e.g., at 614). Further, the non-compliance alert, such as the non-compliance alert 238 of FIG. 2, may be output in response to any of the real-time anesthesia monitoring parameters being non-compliant. For example, the non-compliance alert may be a pop-up alert that is displayed alongside the parameter that is out of compliance. Additionally or alternatively, the one or more computing devices may determine a first number of total active cases that are using the AoA protocol, such as described above at 608, determining a second number of cases using the AoA protocol that are non-compliant with the AoA protocol, and output the non-compliance alert in response to the second number being greater than zero. The non-compliance alert may enable the user to select the case and/or parameter that is out of compliance in order to check the protocol, for example, and make adjustments accordingly.

The method 600 then returns. For example, the method 600 may be repeated as new medical device data is acquired so that the medical data may be stored, processed, and displayed in real-time or in less than real-time, depending on requests received from the user.

Figure 7:
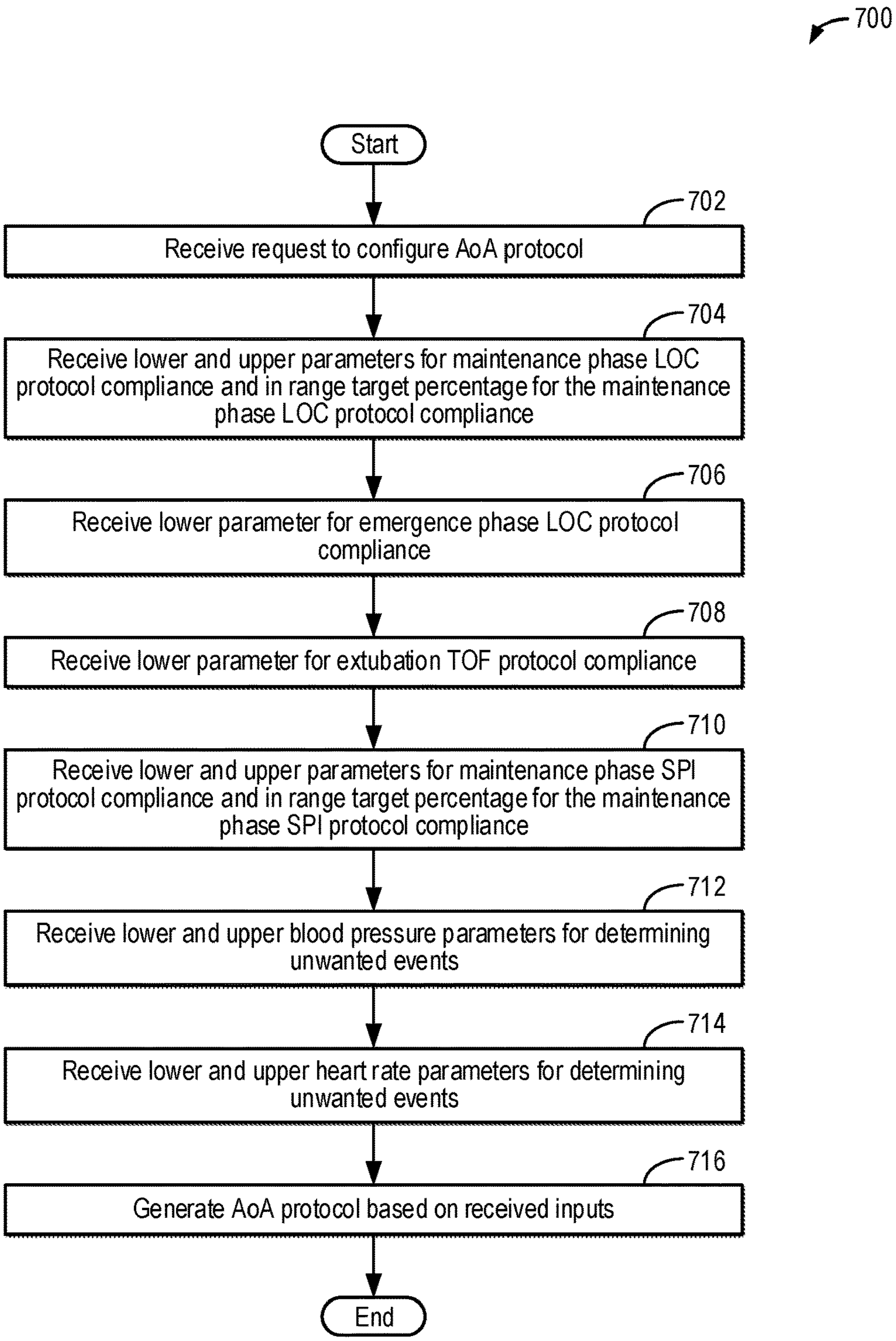
FIG. 7 shows a flow chart for an example method for receiving parameter settings for an AoA protocol via the AoA application.

FIG. 7 shows a flow chart illustrating an example method 700 for using an AoA application to program compliance parameters of an AoA protocol via a corresponding dashboard on a user interface. The AoA application, and thus the method 700, may be implemented by one or more computing devices, such as a care provider device (e.g., care provider device 134 of FIG. 1B) used in combination with an edge device connected to the care provider device (e.g., edge device 20), a cloud in communication with the edge device and/or care provider device (e.g., MDD processing system 12), or any appropriate combination thereof.

At 702, the method 700 includes receiving a request to configure the AoA protocol. For example, a qualified user, such as a supervisor, may input the request to configure the AoA protocol by selecting an AoA administration dashboard of the AoA application, such as the AoA administration dashboard 522 of FIG. 5. The AoA administration dashboard may provide a GUI for receiving a plurality of parameters (e.g., thresholds) that define each aspect of the AoA protocol. For example, the AoA protocol may include a maintenance phase LOC protocol compliance aspect, an emergence phase LOC protocol compliance, a maintenance phase SPI protocol compliance, and an extubation TOF protocol compliance aspect. The AoA protocol may further define unwanted intraoperative heart rate and blood pressure events.

At 704, the method 700 includes receiving lower and upper parameters for the maintenance phase LOC protocol compliance and an in range target percentage for the maintenance phase LOC protocol compliance. For example, via the GUI, the user may select or otherwise enter the lower parameter for the maintenance phase LOC protocol compliance, which defines the lowest maintenance phase LOC value that is considered compliant with the AoA protocol, and select or otherwise enter the upper parameter for the maintenance phase LOC protocol compliance, which defines the highest maintenance phase LOC value that is considered compliant with the maintenance phase LOC aspect of the AoA protocol. Further, the user may select or otherwise enter the in range target percentage for the maintenance phase LOC protocol compliance as a percentage of a total maintenance phase duration for the maintenance phase LOC value to be compliant (e.g., between the upper and lower parameter) for a corresponding case to be considered compliant with the maintenance phase LOC aspect of the AoA protocol, such as described above with respect to FIG. 5.

At 706, the method 700 includes receiving a lower parameter for an emergence phase LOC protocol compliance. For example, via the GUI, the user may select or otherwise enter the lower parameter for the emergence phase LOC protocol compliance, which defines the lowest emergence phase LOC value that is considered compliant with the AoA protocol.

At 708, the method 700 includes receiving a lower parameter for an extubation TOF protocol compliance. For example, via the GUI, the user may select or otherwise enter the lower parameter for the extubation TOF protocol compliance, which defines the lowest extubation TOF value that is considered compliant with the extubation TOF aspect of the AoA protocol.

At 710, the method 700 includes receiving lower and upper parameters for a maintenance phase SPI protocol compliance and an in range target percentage for the maintenance phase SPI protocol compliance. For example, via the GUI, the user may select or otherwise enter the lower parameter for the maintenance phase SPI protocol compliance, which defines the lowest maintenance phase SPI value that is considered compliant with the AoA protocol, and select or otherwise enter the upper parameter for the maintenance phase SPI protocol compliance, which defines the highest maintenance phase SPI value that is considered compliant. Further, the user may select or otherwise enter the in range target percentage for the maintenance phase SPI protocol compliance as a percentage of the total maintenance phase duration. A given clinical gas may be considered to be compliant with the maintenance phase SPI aspect of the AoA protocol when the maintenance phase SPI value is compliant for at least the in range target percentage for the maintenance phase SPI protocol.

The in range target percentage for the maintenance phase SPI protocol compliance may be a same percentage or a different percentage than the in range target percentage for the maintenance phase LOC protocol compliance. For example, the in range target percentage for the maintenance phase LOC protocol compliance may be a first threshold percentage of the total maintenance phase duration, and the in range target percentage for the maintenance phase SPI protocol compliance may be a second threshold percentage of the total maintenance phase duration that is the same or different than the first threshold percentage.

At 712, the method 700 includes receiving lower and upper blood pressure parameters for determining unwanted events. The lower and upper blood pressure parameters may be received from the user via the GUI and may define a target (e.g., desired) blood pressure range. For example, hypotensive events may correspond to blood pressure measurements below the lower blood pressure parameter, and hypertensive events may correspond to blood pressure measurements above the upper blood pressure parameter.

At 714, the method 700 includes receiving lower and upper heart rate parameters for determining unwanted events. The lower and upper heart rate parameters may be received from the user via the GUI and may define a target (e.g., desired) heart rate range. For example, bradycardia events may correspond to heart rate measurements below the lower heart rate parameter, and tachycardia events may correspond to heart rate measurements above the upper heart rate parameter.

At 716, the method 700 includes generating the AoA protocol based on the received inputs. The method 700 may then end. For example, the current AoA protocol may be used until adjusted via a subsequent execution of method 700 by a qualified user.

In this way, the AoA application may facilitate the display of real-time data for a plurality of patients and for a plurality of different patient monitoring parameters and provide readily accessible insights on the tailored anesthesia protocol. For example, data from a plurality of medical devices across a plurality of different operating rooms may be quickly curated, enabling a supervisor to review AoA protocol compliance in real-time or via a historic analysis, which may inform on additional protocol changes or supervisory actions. As a result, anesthetic agent usage may be decreased while unwanted perioperative events are decreased. Further, by helping to deliver an optimal depth of anesthesia via the AoA protocol, an emergence duration may be decreased, allowing for faster patient recovery and reduced procedure times.

A technical effect of an application that displays medical device data aggregated from multiple medical devices on a single graphical user interface that can be switched between real-time data and historic data trends is that a user is able to easily monitor real-time anesthesia parameters for a plurality of patients as well as trends in the anesthesia parameters over time.

The disclosure also provides support for a system, comprising: a display, and a computing device operably coupled to the display and storing instructions executable to: determine each of an adequacy of anesthesia (AoA) protocol usage and an AoA protocol compliance based on medical device data received from one or more medical devices and parameters for an AoA a protocol, and output, to the display, a graphical user interface (GUI) that includes an AoA protocol usage indication generated based on the determined AoA protocol usage and an AoA protocol compliance indication generated based on the determined AoA protocol compliance. In a first example of the system, the AoA protocol usage indication comprises a number of active cases using the AoA protocol relative to a total number of active cases and is displayed via an AoA status dashboard of the GUI. In a second example of the system, optionally including the first example, the AoA protocol usage indication further comprises an AoA icon displayed at an operating room status tile of the AoA status dashboard of the GUI for each operating room having an active case using the AoA protocol, and wherein the operating room status tile further displays one or more real-time anesthesia parameters for each operating room having an active case using the AoA protocol. In a third example of the system, optionally including one or both of the first and second examples, the AoA protocol compliance indication further comprises a real-time non-compliance alert that is displayed via the AoA status dashboard of the GUI for every active case that is not determined have the AoA protocol compliance. In a fourth example of the system, optionally including one or more or each of the first through third examples, the AoA protocol usage indication comprises a first percentage of clinical cases using the AoA protocol out of a total number of the clinical cases within a specified data range and a second percentage of the clinical cases using the AoA protocol that are determined to have the AoA protocol compliance within the specified data range, and wherein the first percentage and the second percentage are displayed via an AoA analysis dashboard of the GUI. In a fifth example of the system, optionally including one or more or each of the first through fourth examples, the AoA protocol compliance indication further comprises individual percentages for protocol compliance in each of a maintenance phase level of consciousness (LOC), a maintenance phase surgical pleth index (SPI), an emergence phase LOC, and an extubation train of four (TOF). In a sixth example of the system, optionally including one or more or each of the first through fifth examples, the computing device stores further instructions executable to: determine a number of unwanted events for a specified data range based on the medical device data received during the specified data range and the parameters for the AoA protocol, and output, to the display, an unwanted events indication for the number of unwanted events for the specified data range via an AoA analysis dashboard of the GUI. In a seventh example of the system, optionally including one or more or each of the first through sixth examples, the unwanted events indication separates the number of unwanted events based on a type of each unwanted event and a AoA protocol compliance status during each unwanted event. In an eighth example of the system, optionally including one or more or each of the first through seventh examples, the computing device stores further instructions executable to: determine an average anesthetic agent cost for a specified data range based on the medical device data received during the specified data range, and output an anesthetic agent cost indication of the average anesthetic agent cost for the specified data range via an AoA analysis dashboard of the GUI. In a ninth example of the system, optionally including one or more or each of the first through eighth examples, the anesthetic agent cost indication separates the average anesthetic agent cost based on a AoA protocol compliance status during each clinical case within the specified data range. In a tenth example of the system, optionally including one or more or each of the first through ninth examples, the computing device stores further instructions executable to: determine an average emergence duration for a specified data range based on the medical device data received during the specified data range, and output an emergence duration indication of the average emergence duration for the specified data range via an AoA analysis dashboard of the GUI. In an eleventh example of the system, optionally including one or more or each of the first through tenth examples, the emergence duration indication separates the average emergence duration based on a AoA protocol compliance status during each clinical case within the specified data range. In a twelfth example of the system, optionally including one or more or each of the first through eleventh examples, the parameters for the AoA protocol include lower and upper bounds for a desired maintenance phase LOC, a lower bound for a desired emergence phase LOC, a lower bound for a desired extubation TOF, lower and upper bounds for a desired maintenance phase SPI, lower and upper bounds for a desired blood pressure measurement, and lower and upper bounds for a desired heart rate measurement, and wherein to determine the AoA protocol compliance, the computing device stores further instructions executable to: analyze the medical device data to determine maintenance phase LOC values, emergence phase LOC values, extubation TOF values, and maintenance phase SPI values for a clinical case, determine that the clinical case has the AoA protocol compliance in response to the maintenance phase LOC values being within the lower and upper bounds for the desired maintenance phase LOC for at least a first threshold percentage of a total maintenance phase, the emergence phase LOC values being greater than the lower bound for the desired emergence phase LOC, the extubation TOF values being greater than the lower bound for the desired extubation TOF, and the maintenance phase SPI values being within the lower and upper bounds for the desired maintenance phase SPI for at least a second threshold percentage of the total maintenance phase, and determine that the clinical case does not have the AoA protocol compliance in response to at least one of maintenance phase LOC values not being within the lower and upper bounds for the desired maintenance phase LOC for at least the first threshold percentage of a total maintenance phase, the emergence phase LOC values not being greater than the lower bound for the desired emergence phase LOC, the extubation TOF values not being greater than the lower bound for the desired extubation TOF, and the maintenance phase SPI values not being within the lower and upper bounds for the desired maintenance phase SPI for at least the second threshold percentage of the total maintenance phase. In a thirteenth example of the system, optionally including one or more or each of the first through twelfth examples, the specified data range comprises data acquired for a selected one or more operating rooms and during a selected time period.

The disclosure also provides support for a method, comprising: receiving settings for an adequacy of anesthesia (AoA) protocol via an AoA administration dashboard of a graphical user interface (GUI), displaying, via the GUI, real-time anesthesia monitoring data determined from a real-time output of one or more medical devices each monitoring a patient in response to an AoA status dashboard being selected via the GUI, and displaying, via the GUI, anesthesia summary data determined from prior data received from the one or more medical devices in response to an AoA analysis dashboard being selected via the GUI. In a first example of the method, receiving the settings for the AoA protocol via the AoA administration dashboard of the GUI comprises receiving, via the GUI, a lower threshold value for a maintenance phase level of consciousness (LOC) compliance aspect of the AoA protocol and an upper threshold value for the maintenance phase LOC compliance aspect of the AoA protocol, and the method further comprises: determining a real-time maintenance phase LOC value from the real-time anesthesia monitoring data, and outputting a non-compliance alert to the AoA status dashboard in response to the real-time maintenance phase LOC value being less than the lower threshold value or greater than the upper threshold value. In a second example of the method, optionally including the first example, receiving the settings for the AoA protocol via the AoA administration dashboard of the GUI comprises receiving, via the GUI, a lower threshold value for an emergence phase LOC compliance aspect of the AoA protocol, and the method further comprises: determining a real-time emergence phase LOC value from the real-time anesthesia monitoring data, and outputting a non-compliance alert to the AoA status dashboard in response to the real-time emergence phase LOC value being less than the lower threshold value. In a third example of the method, optionally including one or both of the first and second examples, receiving the settings for the AoA protocol via the AoA administration dashboard of the GUI comprises receiving, via the GUI, a lower threshold value for an extubation train of four (TOF) compliance aspect of the AoA protocol, and the method further comprises: determining a real-time extubation TOF value from the real-time anesthesia monitoring data, and outputting a non-compliance alert to the AoA status dashboard in response to the real-time extubation TOF value being less than the lower threshold value. In a fourth example of the method, optionally including one or more or each of the first through third examples, receiving the settings for the AoA protocol via the AoA administration dashboard of the GUI comprises receiving, via the GUI, a lower threshold value for a maintenance phase surgical pleth index (SPI) compliance aspect of the AoA protocol and an upper threshold value for the maintenance phase SPI compliance aspect of the AoA protocol, and the method further comprises: determining a real-time maintenance phase SPI value from the real-time anesthesia monitoring data, and outputting a non-compliance alert to the AoA status dashboard in response to the real-time maintenance phase SPI value being less than the lower threshold value or greater than the upper threshold value.

The disclosure also provides support for a system, comprising: a display, and a computing device operably coupled to the display and storing instructions executable to: receive parameters for an adequacy of anesthesia (AoA) protocol via an administrator dashboard of a graphical user interface (GUI) that is output on the display, output real-time AoA protocol compliance data via an AoA status dashboard of the GUI, the AoA protocol compliance summary data comprising at least one of an AoA protocol usage percentage, an AoA protocol usage trend, an AoA protocol compliance percentage, and an AoA protocol compliance trend that are generated for medical device data within a user-specified data range based on the received parameters for the aoa protocol, and output aoa protocol compliance summary data via an AoA analysis dashboard of the GUI. In a first example of the system, the real-time AoA protocol compliance data comprises a first number of active cases using the AoA protocol and a second number of active cases that are using the AoA protocol and non-compliant with the AoA protocol, as determined by comparing real-time medical device data with the received parameters for the AoA protocol, and wherein the computing device stores further instructions executable to: output a non-compliance alert via the GUI in response to the second number being greater than zero.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:

a plurality of medical devices comprising physiological monitoring devices and patient therapy devices at a plurality of medical facilities;

for each medical facility of the plurality of medical facilities, an edge device configured to receive medical device data from each of the plurality of medical devices associated with the medical facility in real-time as time-series data, wherein the edge device encrypts the medical device data;

a display; and a computing device comprising a high-speed ingestion module, a data quality management module, a stream processing engine, an operation case database, and a data lake, wherein the computing device is operably coupled to the display and stores instructions executable to:

receive, at the high-speed ingestion module and from the edge device of each of the plurality of medical facilities, concurrent data streams of the encrypted medical device data at or near a frequency at which the plurality of medical devices output data, wherein the high-speed ingestion module supports ASTMF 2761, wherein the high-speed ingestion module preprocesses the received concurrent data streams of real-time data in time series format;

normalize, enrich, and tag, via the data quality management module, the preprocessed concurrent data streams without impacting data latency, wherein the data quality management module converts units of measure, transforms the medical device data into a canonical data model with metadata, and stores the normalized medical device data in the data lake in a native format;

identify, via the stream processing engine, clinical cases and events from the medical device data;

store the identified clinical cases and events in the operational case database;

determine each of an Adequacy of Anesthesia (AoA) protocol usage and an AoA protocol compliance based on the identified clinical cases and events stored in the operational case database and parameters for an AoA protocol, wherein the parameters for an AoA protocol comprise a range of a clinical measurement, and wherein determining the AoA protocol compliance comprises determining that the clinical measurement is within the range for each of the parameters; and output, to the display, a graphical user interface (GUI) that includes an AoA status dashboard and an AoA analysis dashboard, wherein the AoA status dashboard displays an AoA protocol usage indication generated based on the determined AoA protocol usage, and wherein the GUI includes an AoA protocol compliance indication generated based on the determined AoA protocol compliance;

wherein the physiological monitoring devices comprise heart rate monitors, blood pressure monitors, blood oxygenation monitors, respiration monitors, and electrocardiogram monitors, and wherein the patient therapy devices comprise anesthesia delivery machines;

wherein the high-speed ingestion module of the computing device is configured to ingest increased bandwidth of the medical device data without significant decrease in ingestion speeds;

wherein the parameters for the AoA protocol include lower and upper bounds for a desired maintenance phase level of consciousness (LOC), a lower bound for a desired emergence phase LOC, a lower bound for a desired extubation train of four (TOF), lower and upper bounds for a desired maintenance phase surgical pleth index (SPI), and wherein to determine the AoA protocol compliance, the computing device stores further instructions executable to:

analyze the medical device data to determine maintenance phase LOC values, emergence phase LOC values, extubation TOF values, and maintenance phase SPI values for each clinical case;

determine that the clinical case has the AoA protocol compliance in response to the maintenance phase LOC values being within the lower and upper bounds for the desired maintenance phase LOC for at least a first threshold percentage of a total maintenance phase, the emergence phase LOC values being greater than the lower bound for the desired emergence phase LOC, the extubation TOF values being greater than the lower bound for the desired extubation TOF, and the maintenance phase SPI values being within the lower and upper bounds for the desired maintenance phase SPI for at least a second threshold percentage of the total maintenance phase; and determine that the clinical case does not have the AoA protocol compliance in response to at least one of maintenance phase LOC values not being within the lower and upper bounds for the desired maintenance phase LOC for at least the first threshold percentage of a total maintenance phase, the emergence phase LOC values not being greater than the lower bound for the desired emergence phase LOC, the extubation TOF values not being greater than the lower bound for the desired extubation TOF, and the maintenance phase SPI values not being within the lower and upper bounds for the desired maintenance phase SPI for at least the second threshold percentage of the total maintenance phase;

wherein the AoA status dashboard of the GUI comprises an operating room status tile for each operating room having an active case using the AoA protocol; and wherein the computing device stores further instructions executable to display a real-time non-compliance alert on the operating room status tile in response to determining that the clinical case associated with the operating room status tile does not have the AoA protocol compliance.

2. The system of claim 1, wherein the AoA protocol usage indication comprises a number of active cases using the AoA protocol relative to a total number of active cases, wherein the AoA analysis dashboard displays AoA protocol compliance summary data, and wherein the AoA protocol compliance summary data comprises at least one of an AoA protocol usage percentage, an AoA protocol usage trend, an AoA protocol compliance percentage, and an AoA protocol compliance trend that are generated for medical device data within a user-specified data range based on the parameters for the AoA protocol.

3. The system of claim 1, wherein the AoA protocol usage indication further comprises an AoA icon displayed at the operating room status tile of the AoA status dashboard of the GUI for each operating room having an active case using the AoA protocol, and wherein the operating room status tile further displays one or more real-time anesthesia monitoring data for each operating room having an active case using the AoA protocol; and wherein the parameters for the AoA protocol are received via an administrator dashboard of the GUI.

4. The system of claim 1, wherein the AoA protocol usage indication comprises a first percentage of clinical cases using the AoA protocol out of a total number of the clinical cases within a specified data range and a second percentage of the clinical cases using the AoA protocol that are determined to have the AoA protocol compliance within the specified data range, and wherein the first percentage and the second percentage are displayed via an AoA analysis dashboard of the GUI.

5. The system of claim 4, wherein the AoA protocol compliance indication further comprises individual percentages for protocol compliance in each of the parameters.

6. The system of claim 1, wherein the computing device stores further instructions executable to:

determine a number of unwanted events for a specified data range based on the medical device data received during the specified data range and the parameters for the AoA protocol; and output, to the display, an unwanted events indication for the number of unwanted events for the specified data range via an AoA analysis dashboard of the GUI.

7. The system of claim 6, wherein the unwanted events indication separates the number of unwanted events based on a type of each unwanted event and a AoA protocol compliance status during each unwanted event.

8. The system of claim 1, wherein the computing device stores further instructions executable to:

determine an average anesthetic agent cost for a specified data range based on the medical device data received during the specified data range; and output an anesthetic agent cost indication of the average anesthetic agent cost for the specified data range via an AoA analysis dashboard of the GUI.

9. The system of claim 8, wherein the anesthetic agent cost indication separates the average anesthetic agent cost based on a AoA protocol compliance status during each clinical case within the specified data range.

10. The system of claim 1, wherein the computing device stores further instructions executable to:

determine an average emergence duration for a specified data range based on the medical device data received during the specified data range; and output an emergence duration indication of the average emergence duration for the specified data range via an AoA analysis dashboard of the GUI.

11. The system of claim 10, wherein the emergence duration indication separates the average emergence duration based on a AoA protocol compliance status during each clinical case within the specified data range.

12. The system of claim 1, wherein the parameters for the AoA protocol further include lower and upper bounds for a desired blood pressure measurement, and lower and upper bounds for a desired heart rate measurement.

13. A method, comprising:

receiving parameters for an Adequacy of Anesthesia (AoA) protocol via an AoA administration dashboard of a graphical user interface (GUI), wherein receiving the parameters for the AoA protocol comprises:

receiving a maintenance phase level of consciousness (LOC) lower parameter;

receiving a maintenance phase LOC upper parameter;

receiving a maintenance phase LOC in range target percentage;

receiving an emergence phase LOC lower parameter;

receiving an extubation train of four (TOF) lower parameter;

receiving a maintenance phase surgical pleth index (SPI) lower parameter;

receiving a maintenance phase SPI upper parameter;

receiving a maintenance phase SPI in range target percentage;

receiving a blood pressure lower parameter;

receiving a blood pressure upper parameter;

receiving a heart rate lower parameter;

receiving a heart rate upper parameter;

generating the AoA protocol based on the maintenance phase LOC lower parameter, the maintenance phase LOC upper parameter; the maintenance phase LOC in range target percentage, the emergence phase LOC lower parameter, the extubation TOF lower parameter, the maintenance phase SPI lower parameter, the maintenance phase SPI upper parameter, the maintenance phase SPI in range target percentage, the blood pressure lower parameter, the blood pressure upper parameter, the heart rate lower parameter, and the heart rate upper parameter;

receiving, by a plurality of edge devices each located at a medical facility of a plurality of medical facilities, real-time anesthesia monitoring data, wherein the real-time anesthesia monitoring data comprises a real-time output from a plurality of medical devices each monitoring a patient, and wherein the plurality of medical devices comprises physiological monitoring devices and patient therapy devices;

continuously transmitting, by the plurality of edge devices, the real-time monitoring data as de-identified data in a time series format over an encrypted communication channel;

receiving, at a high-speed ingestion module, concurrent data streams of the real-time monitoring data transmitted by the plurality of edge devices at or near the frequency at which the plurality of medical devices output data;

normalizing and enriching, via a data quality management module, the concurrent data streams without impacting data latency, wherein the data quality management module converts units of measure, transforms the concurrent data streams into a canonical data model with metadata, and stores the concurrent data streams in the data lake in a native format;

identifying, via a stream processing engine, clinical cases and events from the concurrent data streams;

storing the identified clinical cases and events in an operational case database;

ingesting increased bandwidth of the real-time monitoring data without significant decrease in ingestion speeds;

determining AoA protocol usage and AoA protocol compliance based on the identified clinical cases and events stored in the operational case database;

displaying, via the GUI, an AoA protocol usage indication and an AoA protocol compliance indication for each operating room having an active case in response to an AoA status dashboard being selected via the GUI, the AoA protocol usage indication based on the AoA protocol usage and the AoA protocol compliance indication based on the AoA protocol compliance; and displaying, via the GUI, anesthesia summary data determined from prior data received from the one or more medical devices in response to an AoA analysis dashboard being selected via the GUI.

14. The method of claim 13, wherein, for a specified data range, the AoA analysis dashboard of the GUI displays an unwanted events indication of a sum of unwanted events, an emergence duration indication of an average emergence duration, and an anesthetic agent cost indication of an average anesthetic agent cost; and wherein receiving the parameters for the AoA protocol via the AoA administration dashboard of the GUI comprises receiving, via the GUI, a lower threshold value for a maintenance phase level of consciousness (LOC) compliance aspect of the AoA protocol and an upper threshold value for the maintenance phase LOC compliance aspect of the AoA protocol, and the method further comprises:

determining a real-time maintenance phase LOC value from the real-time anesthesia monitoring data; and outputting a non-compliance alert to the AoA status dashboard in response to the real-time maintenance phase LOC value being less than the lower threshold value or greater than the upper threshold value.

15. The method of claim 13, wherein receiving the parameters for the AoA protocol via the AoA administration dashboard of the GUI comprises receiving, via the GUI, a lower threshold value for an emergence phase LOC compliance aspect of the AoA protocol, and the method further comprises:

determining a real-time emergence phase LOC value from the real-time anesthesia monitoring data; and outputting a non-compliance alert to the AoA status dashboard in response to the real-time emergence phase LOC value being less than the lower threshold value.

16. The method of claim 13, wherein receiving the parameters for the AoA protocol via the AoA administration dashboard of the GUI comprises receiving, via the GUI, a lower threshold value for an extubation train of four (TOF) compliance aspect of the AoA protocol, and the method further comprises:

determining a real-time extubation TOF value from the real-time anesthesia monitoring data; and outputting a non-compliance alert to the AoA status dashboard in response to the real-time extubation TOF value being less than the lower threshold value.

17. The method of claim 13, wherein receiving the parameters for the AoA protocol via the AoA administration dashboard of the GUI comprises receiving, via the GUI, a lower threshold value for a maintenance phase surgical pleth index (SPI) compliance aspect of the AoA protocol and an upper threshold value for the maintenance phase SPI compliance aspect of the AoA protocol, and the method further comprises:

determining a real-time maintenance phase SPI value from the real-time anesthesia monitoring data; and outputting a non-compliance alert to the AoA status dashboard in response to the real-time maintenance phase SPI value being less than the lower threshold value or greater than the upper threshold value.

18. A system, comprising:

a display; and a computing device comprising a high-speed ingestion module, a data quality management module, a stream processing engine, an operation case database, and a data lake, the computing device operably coupled to the display and storing instructions executable to:

receive parameters for an Adequacy of Anesthesia (AoA) protocol via an administrator dashboard of a graphical user interface (GUI) that is output on the display;

receive, at the high-speed ingestion module, concurrent data streams from a plurality of medical devices across multiple sites at or near a frequency at which medical devices of the plurality of medical devices can output data, wherein the plurality of medical devices comprise physiological monitoring devices and patient therapy devices, the concurrent data streams of time-series data received from edge devices;

enrich and normalize, via the data quality management module, the received concurrent data streams without impacting data latency, wherein the data quality management module converts units of measure, transforms data into a canonical data model with metadata, and stores the enriched and normalized concurrent data streams in the data lake in a native format;

identify, via the stream processing engine, clinical cases and events from the concurrent data streams;

store the identified clinical cases and events in the operational case database;

use the clinical cases and events stored in the operational cases database to determine real-time AoA protocol compliance data;

output an AoA protocol usage indication and an AoA protocol compliance indication based on the real-time AoA protocol compliance data via an AoA status dashboard of the GUI; and output AoA protocol compliance summary data via an AoA analysis dashboard of the GUI, the AoA protocol compliance summary data comprising at least one of an AoA protocol usage percentage, an AoA protocol usage trend, an AoA protocol compliance percentage, and an AoA protocol compliance trend that are generated for medical device data within a user-specified data range based on the received parameters for the AoA protocol;

wherein the AoA protocol usage indication comprises an AoA icon displayed at an operating room status tile for each operating room having an active case using the AoA protocol, and wherein the operating room status tile further displays the real-time AoA protocol compliance data; wherein the AoA protocol compliance percentage comprises individual percentages for protocol compliance in each of a maintenance phase level of consciousness (LOC), a maintenance phase surgical pleth index (SPI), an emergence phase LOC, and an extubation train of four (TOF); wherein, for a specified data range, the AoA analysis dashboard of the GUI displays an unwanted events indication of a sum of unwanted events, an emergence duration indication of an average emergence duration, and an anesthetic agent cost indication of an average anesthetic agent cost; wherein the real-time AoA protocol compliance data comprises a first number of active cases using the AoA protocol and a second number of active cases that are using the AoA protocol and non-compliant with the AoA protocol, as determined by comparing real-time medical device data with the received parameters for the AoA protocol; and wherein the computing device stores further instructions executable to:

generate and display a non-compliance alert via the GUI in response to the second number being greater than zero; and wherein the computing device is scalable to ingest increased bandwidth without significant decrease in ingestion speeds.

* * * * *